United States Patent
Bhandarkar et al.

(10) Patent No.: US 7,420,085 B2
(45) Date of Patent: Sep. 2, 2008

(54) POLYMORPHS OF SODIUM 4-[(4-CHLORO-2-HYDROXYBENZOYL) AMINO] BUTANOATE

(75) Inventors: Satej Bhandarkar, Downingtown, PA (US); Shingai Majuru, Brewster, NY (US); Halina Levchik, Croton on Hudson, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 0 days.

(21) Appl. No.: 11/734,591

(22) Filed: Apr. 12, 2007

(65) Prior Publication Data

US 2008/0033204 A1 Feb. 7, 2008

Related U.S. Application Data

(63) Continuation-in-part of application No. 10/501,205, filed as application No. PCT/US03/00878 on Jan. 9, 2003, now Pat. No. 7,227,033, application No. 11/734, 591, filed on Jul. 14, 2005, which is a continuation-in-part of application No. 10/312,703, filed as application No. PCT/US01/21073 on Jun. 29, 2001.

(60) Provisional application No. 60/347,610, filed on Jan. 9, 2002, provisional application No. 60/214,893, filed on Jun. 29, 2000.

(51) Int. Cl.
C07C 229/00 (2006.01)

(52) U.S. Cl. .................. 562/450; 562/452
(58) Field of Classification Search .............. None
See application file for complete search history.

(56) References Cited

U.S. PATENT DOCUMENTS

| 5,643,957 | A * | 7/1997 | Leone-Bay et al. | 514/563 |
| 7,208,178 | B2 * | 4/2007 | Bhandarkar et al. | 424/489 |
| 7,227,033 | B2 * | 6/2007 | Bhandarkar et al. | 562/450 |
| 2004/0048777 | A1 * | 3/2004 | Weidner et al. | 514/2 |
| 2005/0250852 | A1 * | 11/2005 | Bhandarkar et al. | 514/563 |
| 2005/0272639 | A1 * | 12/2005 | Bhandarkar et al. | 514/3 |
| 2007/0161708 | A1 * | 7/2007 | Bhandarkar et al. | 514/563 |

FOREIGN PATENT DOCUMENTS

| WO | 98/34632 | 8/1998 |
| WO | 00/46182 | 8/2000 |
| WO | 02/02509 A1 | 1/2002 |

OTHER PUBLICATIONS

Declaration Under 37 C.F.R. 1.132 of Halina Levchik, Ph.D., with Exhibits A-I, Jun. 8, 2006.

* cited by examiner

*Primary Examiner*—Yvonne Eyler
*Assistant Examiner*—MLouisa Lao
(74) *Attorney, Agent, or Firm*—Darby & Darby P.C.

(57) ABSTRACT

The present invention relates to amorphous and polymorphic forms of sodium 4-[(4-chloro-2-hydroxybenzoyl)amino]butanoate and their use for facilitating the delivery of active agents, such as insulin, to a target.

11 Claims, 31 Drawing Sheets

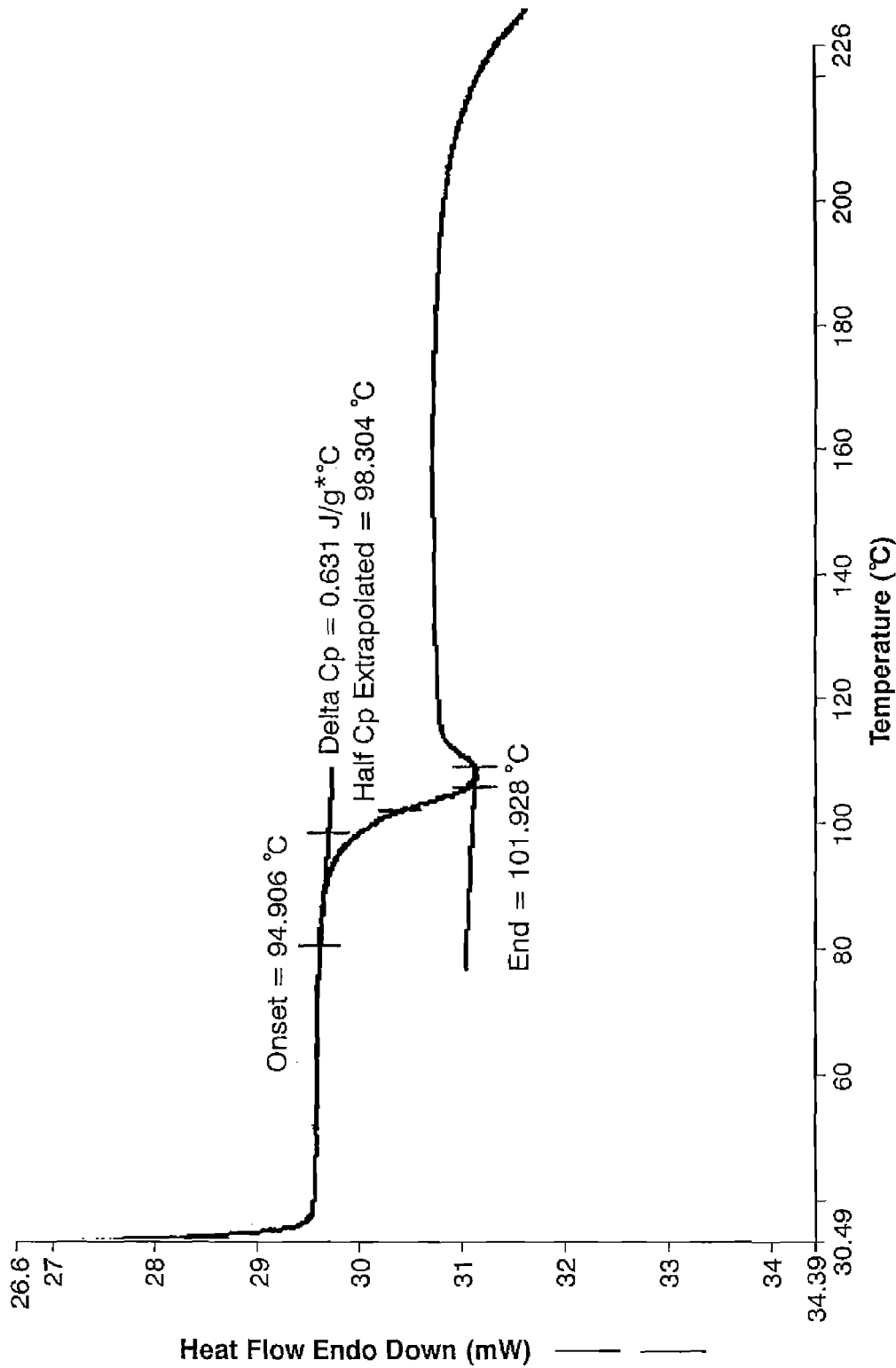

POLYMORPHS OF SODIUM 4-[(4-CHLORO-2-HYDROXYBENZOYL) AMINO] BUTANOATE

This application is (1) a continuation of U.S. Ser. No. 10/501,205, filed Jul. 9, 2004, now U.S. Pat. No. 7,227,033 which is a national phase of International Patent Application No. PCT/US03/00878, filed Jan. 9, 2003 and published in English as International Publication No. WO 03/057650, which claims the benefit of U.S. Provisional Application No. 60/347,610 filed Jan. 9, 2002, and (2) is a continuation-in-part of U.S. Ser. No. 10/312,703, filed Jun. 25, 2003, now U.S. Pat. No. 7,351,741 which is a national phase of International Patent Application No. PCT/US01/21073, filed Jun. 29, 2001 and published in English as International Publication No. WO 02/02509, which claims the benefit of U.S. Provisional Application No. 60/214,893, filed Jun. 29, 2000. These prior applications are hereby incorporated by reference in their entirety.

FIELD OF THE INVENTION

The present invention relates to amorphous and polymorphic forms of sodium 4-[(4-chloro-2-hydroxybenzoyl) amino] butanoate and compositions containing the same for delivering active agents to a target. These compounds are well suited for forming non-covalent mixtures with active agents for oral, intracolonic, pulmonary, or other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; 5,866,536 and International Patent Publication Nos., WO 00/07979, WO 00/50386, WO 01/132130 and WO 01/132596.

More recently, a polymer has been conjugated to a modified amino acid or a derivative thereof via a linkage group to provide for polymeric delivery agents. The modified polymer may be any polymer, but preferred polymers include, but are not limited to, polyethylene glycol (PEG), and derivatives thereof. See, for example, International Publication No. WO 00/40203.

International Publication No. WO 02/02509 discloses 4-[(4-chloro, 2-hydroxybenzoyl)amino]butanoic acid (4-CNAB) as an agent for facilitating the delivery of biologically active agents.

SUMMARY OF THE INVENTION

The present invention relates to five crystalline forms and an amorphous form of sodium 4-[(4-chloro, 2-hydroxybenzoyl)amino]butanoate (hereinafter "sodium 4-CNAB"), which has the following structure:

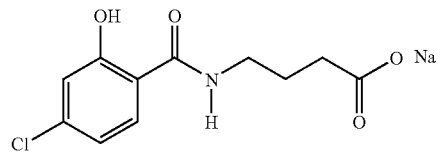

and for processes for their preparation. The five crystalline polymorphs are herein referred to as Forms I-V. Forms I-V have X-ray powder diffractograms (XRPDs) substantially identical to that shown in FIGS. 1-5, respectively. The amorphous form typically has an XRPD substantially as shown in FIG. 28.

The present invention also relates to a method of treating type I or type II diabetes in an animal (such as a human) in need thereof, comprising administering to the animal a therapeutic effective amount of a composition comprising insulin and one or more forms of sodium 4-CNAB of the present invention. The sodium 4-CNAB facilitates insulin transport in a therapeutically effective amount. Preferably, the composition is a dosage form for oral administration. More preferably, the composition is a solid oral dosage form.

This invention further relates to the oral delivery of therapeutic active agents, including proteins, in a therapeutically effective amount in the bloodstream. Such proteins may be used as part of a therapeutic regimen.

BRIEF DESCRIPTION OF THE DRAWINGS

FIGS. 27A and 27B are DSC scans of amorphous sodium 4-CNAB.

DETAILED DESCRIPTION OF THE INVENTION

Definitions

Figure 1:
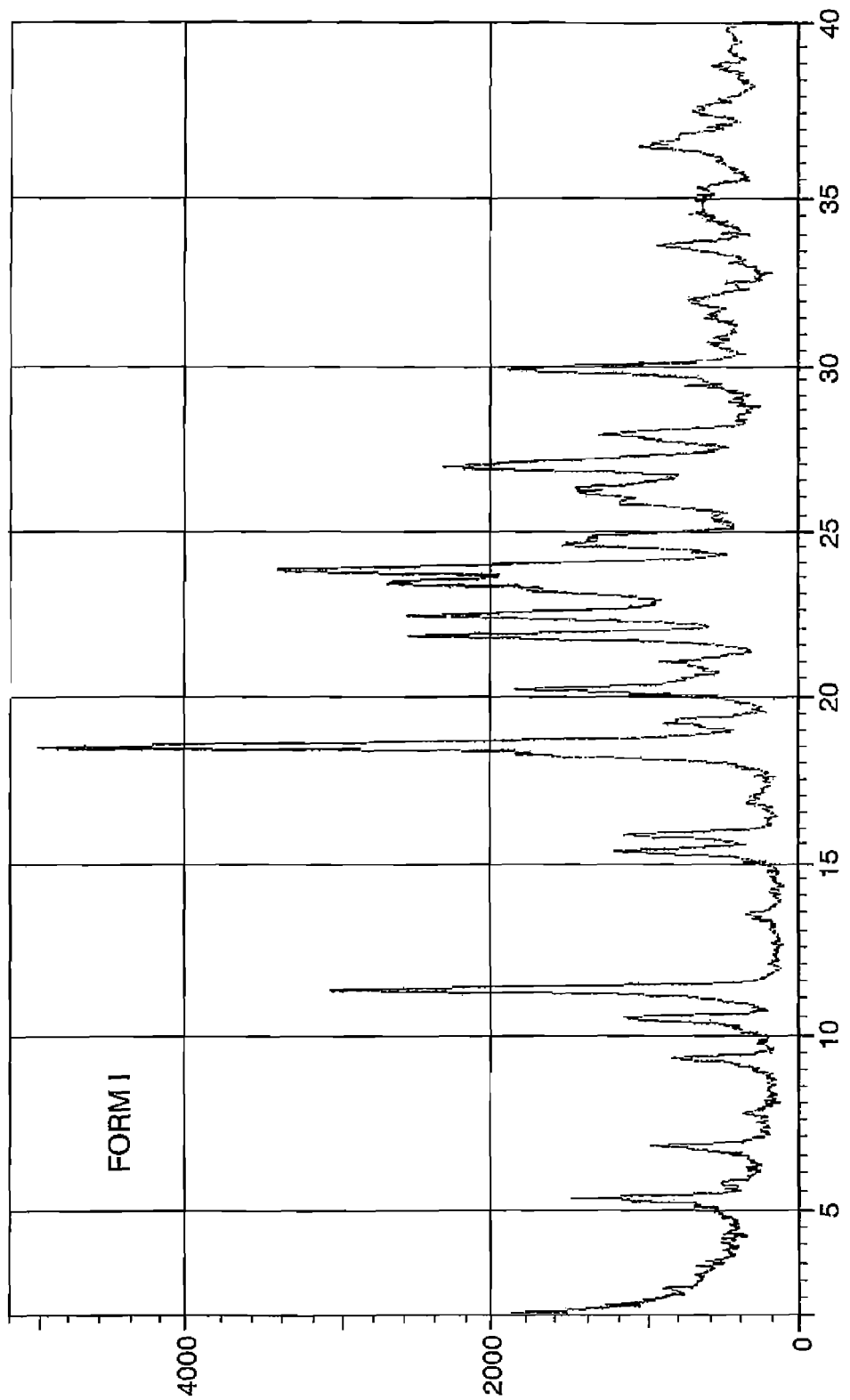
FIGS. 1-5 are X-ray powder diffractograms (XRPDs) of Forms I-V of sodium 4-CNAB, respectively.

The term "crystal" refers to a form of a solid state of matter, which is distinct from its amorphous solid state. Crystals display characteristic features including a lattice structure, characteristic shapes and optical properties such as refractive index. A crystal consists of atoms arranged in a pattern that repeats periodically in three dimensions.

The term "polymorph" refers to crystallographically distinct forms of a substance.

The term "hydrate" as used herein includes, but is not limited to, (i) a substance containing water combined in the molecular form and (ii) a crystalline substance containing one or more molecules of water of crystallization or a crystalline material containing free water.

The term "hemihydrate" refers to a hydrate where every molecule of water is associated with two molecules of sodium 4-CNAB.

The term "pentahydrate" refers to a hydrate where each molecule of sodium 4-CNAB is associated with five molecules of water.

The term "solvate" as used herein includes, but is not limited to, a molecular or ionic complex of molecules or ions of a solvent with molecules or ions of sodium 4-CNAB.

The term "delivery agent" refers to sodium 4-CNAB, including its amorphous and crystalline polymorphic forms.

An "effective amount of drug" is an amount of the active agent (e.g., cromolyn sodium) which is effective to treat or prevent a condition in a living organism to whom it is administered over some period of time, e.g., provides a therapeutic effect during a desired dosing interval.

An "effective amount of delivery agent" is an amount of the Delivery Agent which promotes the absorption of a desired amount of the active agent via any route of administration (such as those discussed in this application including, but not limited to, the oral (e.g., across a biological membrane in the gastrointestinal tract), nasal, pulmonary, dermal, vaginal, and/or ocular route).

The term "insulin" refers to all forms of insulin, including, but not limited to, naturally derived insulin and synthetic forms of insulin, such as those described in U.S. Pat. Nos. 4,421,685, 5,474,978, and 5,534,488, each of which is hereby incorporated by reference in its entirety.

The term "AUC" as used herein, means area under the plasma concentration-time curve, as calculated by the trapezoidal rule over the complete dosing interval, e.g., 24-hour interval.

The term "mean", when preceding a pharmacokinetic value (e.g., mean Peak) represents the arithmetic mean value of the pharmacokinetic value unless otherwise specified.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "sodium 4-CNAB" refers to sodium 4-[(4-chloro-2-hydroxybenzoyl)amino]butanoate, which is also known as monosodium N-(4-chlorosalicyloyl)-4-aminobutyrate. Unless otherwise noted, the term "4-CNAB" as used herein refers to racemic mixtures and optically pure enantiomers of 4-CNAB. The crystalline polymorphs of the present invention may be racemic mixtures or optically pure enantiomers of sodium 4-CNAB.

The term "about" generally means within 10%, preferably within 5%, and more preferably within 1% of a given value or range.

Preparation of Sodium 4-CNAB

The free acid and sodium salt of 4-CNAB may be prepared as described in International Publication No. WO 02/02509, which is hereby incorporated by reference. They may also be prepared by the methods described in International Publication Nos. 00/46182 and 01/70219, which are both hereby incorporated by reference.

Sodium 4-CNAB may be prepared from the free acid of 4-CNAB by methods known in the art. For example, sodium 4-CNAB may be prepared by dissolving the free acid of 4-CNAB in ethanol and adding aqueous sodium hydroxide. Typically, the molar ratio of sodium hydroxide to the free acid is about 1:1.

The compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Form I

The term "Form I" as used herein refers to an anhydrous crystalline polymorph of sodium 4-CNAB having an XRPD pattern substantially identical to that shown in FIG. 1. Peak locations (in degrees 2Θ±0.2, 0.1, 0.05, or 0.01° 2Θ) for the XRPD pattern in FIG. 1 are provided in Table A below. Form I has a melting point onset as determined by DSC at about 218-219° C.

TABLE A

| 2-theta | d (Å) |
|---|---|
| 5.26 | 16.77 |
| 5.68 | 15.55 |
| 6.75 | 13.09 |
| 7.70 | 11.47 |
| 9.28 | 9.52 |
| 10.04 | 8.8 |
| 10.43 | 8.47 |
| 10.92 | 8.10 |
| 11.29 | 7.83 |
| 13.41 | 6.60 |
| 15.32 | 5.78 |
| 15.81 | 5.60 |
| 18.12 | 4.89 |
| 18.51 | 4.79 |
| 19.16 | 4.63 |
| 19.8 | 4.48 |
| 20.17 | 4.40 |
| 20.88 | 4.25 |
| 21.78 | 4.08 |
| 22.41 | 3.96 |
| 23.08 | 3.85 |
| 23.4 | 3.80 |
| 23.79 | 3.74 |
| 24.56 | 3.62 |
| 24.76 | 3.59 |
| 25.8 | 3.45 |
| 26.2 | 3.40 |
| 26.91 | 3.31 |
| 27.79 | 3.21 |
| 29.28 | 3.05 |
| 29.79 | 3.00 |
| 30.08 | 2.97 |
| 30.62 | 2.92 |
| 31.36 | 2.85 |
| 31.86 | 2.81 |
| 32.32 | 2.77 |
| 33.00 | 2.71 |
| 33.46 | 2.68 |
| 34.12 | 2.63 |

In particular, the peaks (expressed in degrees 2Θ±0.2° 2Θ) at 5.2, 11.2, 15.7, 18.5, 20.1, 21.8, 23.4, 23.8, 26.9, and 29.8 are unique to Form I.

Form I of sodium 4-CNAB may be prepared by sequentially (a) dissolving the free acid of 4-CNAB in an organic solvent (e.g., acetone, methanol, ethanol, or a mixture thereof or with water), (b) adding sodium hydroxide or other sodium source (such as sodium alkoxides and sodium hydride) to the solution (preferably the molar ratio of sodium ions to free acid of 4-CNAB is about 1:1), (c) heating the solution to reflux (e.g., to about 60° C.), (d) cooling the solution, and (e) optionally, recovering the crystals of sodium 4-CNAB (e.g., by vacuum filtration. Form I may also be prepared by heating one or both of Forms II and IV above their solid state transition temperature.

Form II

Figure 2:
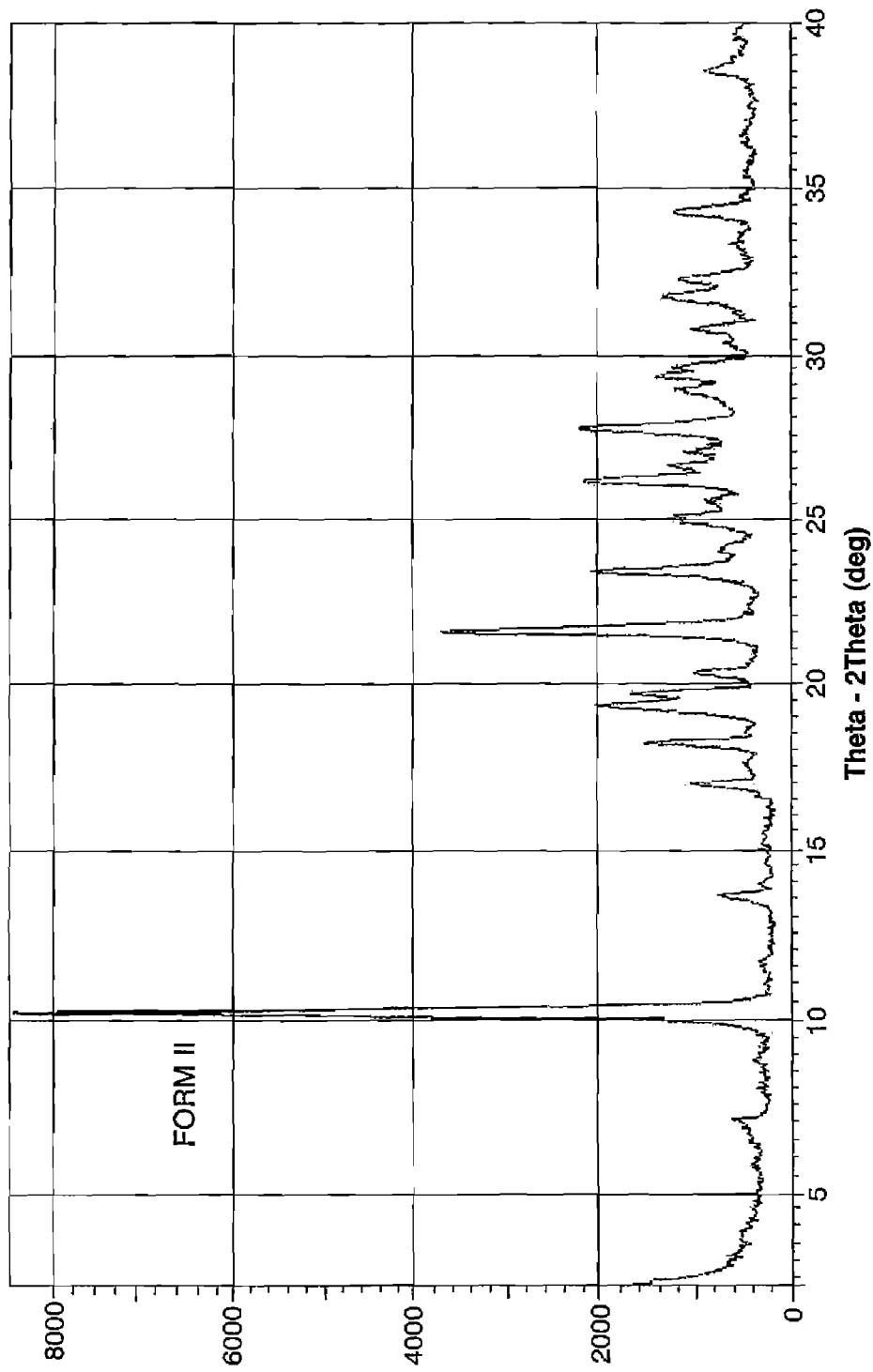

The term "Form II" as used herein refers to a crystalline polymorph of a hydrate of sodium 4-CNAB having an XRPD pattern substantially identical to that shown in FIG. 2. Peak locations (in degrees 2Θ±0.2, 0.1, 0.05, or 0.01° 2Θ) for the XRPD pattern in FIG. 2 are provided in Table B below. Form II exhibits a melting point onset as determined by DSC at about 214.24° C. Form II converts to Form I upon being heated to about 170-180° C. Form I then begins to melt at about 214.24° C.

TABLE B

| 2-theta | d (Å) |
|---|---|
| 6.77 | 13.05 |
| 9.72 | 9.09 |
| 10.22 | 8.65 |
| 13.59 | 6.51 |
| 17.02 | 5.2 |
| 18.29 | 4.85 |
| 19.48 | 4.55 |
| 19.8 | 4.48 |
| 20.44 | 4.34 |
| 21.4 | 4.15 |
| 21.76 | 4.08 |
| 23.54 | 3.78 |
| 24.16 | 3.68 |
| 25.10 | 3.55 |
| 25.64 | 3.47 |
| 26.29 | 3.39 |
| 26.67 | 3.34 |
| 27.07 | 3.29 |
| 27.82 | 3.20 |
| 28.97 | 3.08 |
| 29.4 | 3.04 |
| 29.68 | 3.01 |
| 30.81 | 2.90 |
| 31.78 | 2.81 |
| 32.28 | 2.77 |
| 34.30 | 2.61 |
| 38.50 | 2.34 |
| 41.56 | 2.17 |
| 41.76 | 2.16 |
| 44.98 | 2.01 |
| 46.98 | 1.93 |

In particular, the peaks (expressed in degrees 2Θ±0.2° 2Θ) at 10.2, 18.3, 19.5, 19.8, 21.8, 23.5, 26.3, 27.8, 29.4, and 31.8 are unique to Form II.

Form II of sodium 4-CNAB may be prepared by sequentially (a) dissolving the free acid of 4-CNAB in water, (b) adding sodium hydroxide to the solution, (c) optionally, heating the solution, and (d) optionally, recovering the crystals of sodium 4-CNAB in the solution of step (b) or (c). Form II may also be prepared by exposing one or more of Forms III and V and the amorphous form of sodium 4-CNAB to moisture. Yet another method of preparing Form II is by drying Form IV in a low humidity environment (e.g., an environment having less than about 55% relative humidity).

Form III

Figure 3:
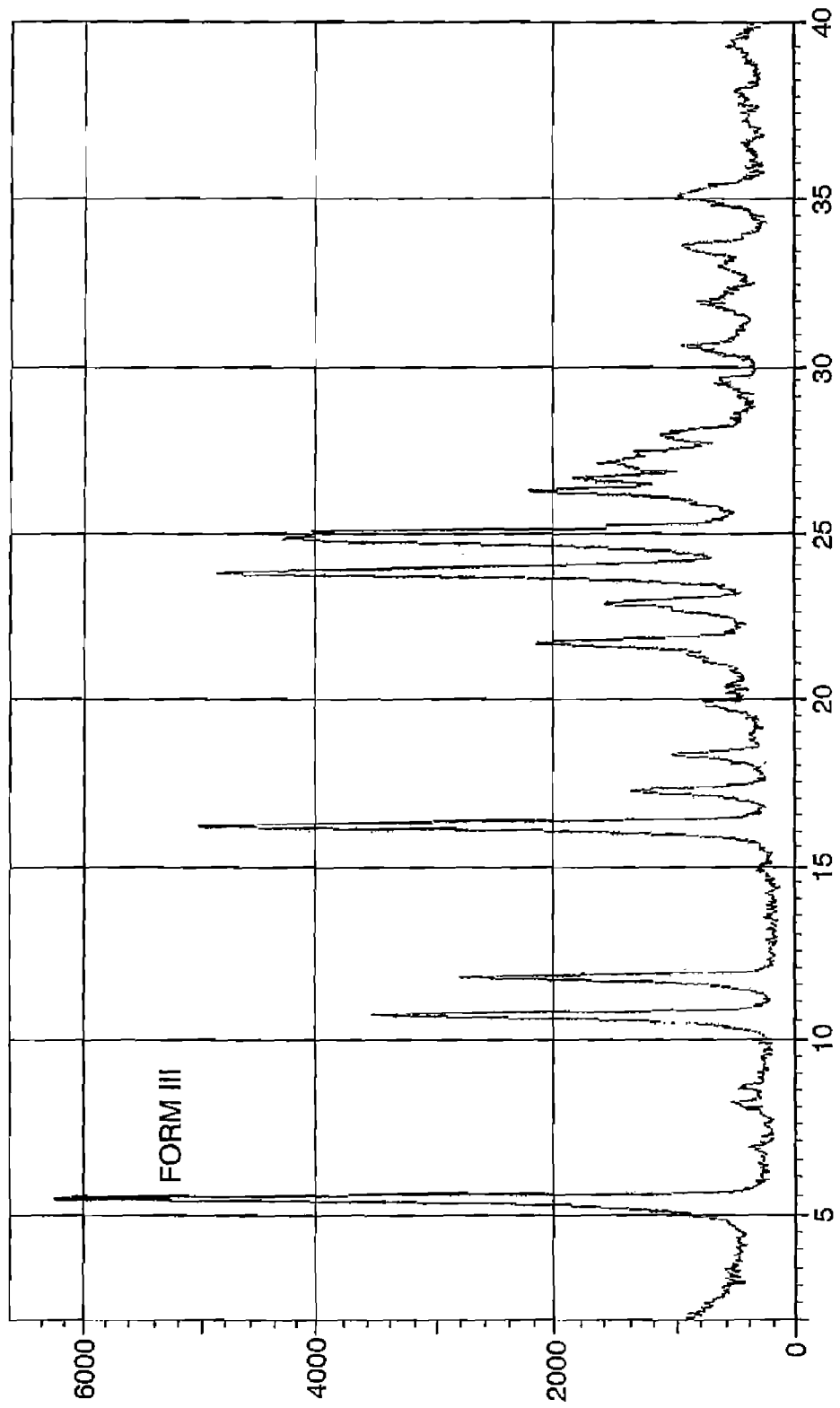

The term "Form III" as used herein refers to a crystalline polymorph of an isopropanol monosolvate of sodium 4-CNAB having an XRPD pattern substantially identical to that shown in FIG. 3. Peak locations (in degrees 2Θ+/−0.2, 0.1, 0.05, or 0.01° 2Θ) for the XRPD pattern in FIG. 3 are provided in Table C below. Form III exhibits a melting point onset as determined by DSC at about 223.08° C. Form III converts to Form V upon being heated to about 130° C. Form V then begins to melt at about 223.08° C.

TABLE C

| 2-theta | d (Å) |
|---|---|
| 4.72 | 18.71 |
| 5.41 | 16.31 |
| 8.15 | 10.83 |
| 10.78 | 8.2 |
| 11.52 | 7.68 |
| 11.86 | 7.45 |
| 15.88 | 5.58 |
| 16.28 | 5.44 |
| 17.28 | 15.13 |

TABLE C-continued

| 2-theta | d (Å) |
|---|---|
| 18.34 | 4.83 |
| 19.80 | 4.48 |
| 21.00 | 4.23 |
| 21.24 | 4.18 |
| 21.62 | 4.11 |
| 22.56 | 3.94 |
| 22.76 | 3.90 |
| 23.69 | 3.75 |
| 24.64 | 3.61 |
| 25.00 | 3.56 |
| 26.03 | 3.42 |
| 26.38 | 3.38 |
| 26.81 | 3.32 |
| 27.16 | 3.28 |
| 27.6 | 3.23 |
| 27.8 | 3.21 |
| 28.96 | 3.08 |
| 29.32 | 3.04 |
| 30.20 | 2.96 |
| 30.36 | 2.94 |
| 31.47 | 2.84 |
| 32.54 | 2.75 |
| 32.88 | 2.72 |
| 33.08 | 2.71 |
| 34.55 | 2.59 |
| 34.96 | 2.56 |
| 37.51 | 2.40 |
| 40.00 | 2.25 |
| 40.18 | 2.24 |
| 40.44 | 2.23 |

In particular, the peaks (expressed in degrees 2Θ±0.2° 2Θ) at 5.5, 10.8, 11.9, 16.3, 17.3, 21.7, 24.7, 25.0, 26.1, and 26.4 are unique to Form III.

Form III may be prepared by sequentially (a) dissolving the free acid of 4-CNAB in isopropanol, (b) heating the solution to above room temperature (and preferably to about 62° C.), (c) adding sodium hydroxide to the solution, (d) heating the solution to reflux, (e) cooling the solution, and, optionally, (f) recovering the crystals of sodium 4-CNAB.

Form IV

Figure 4:
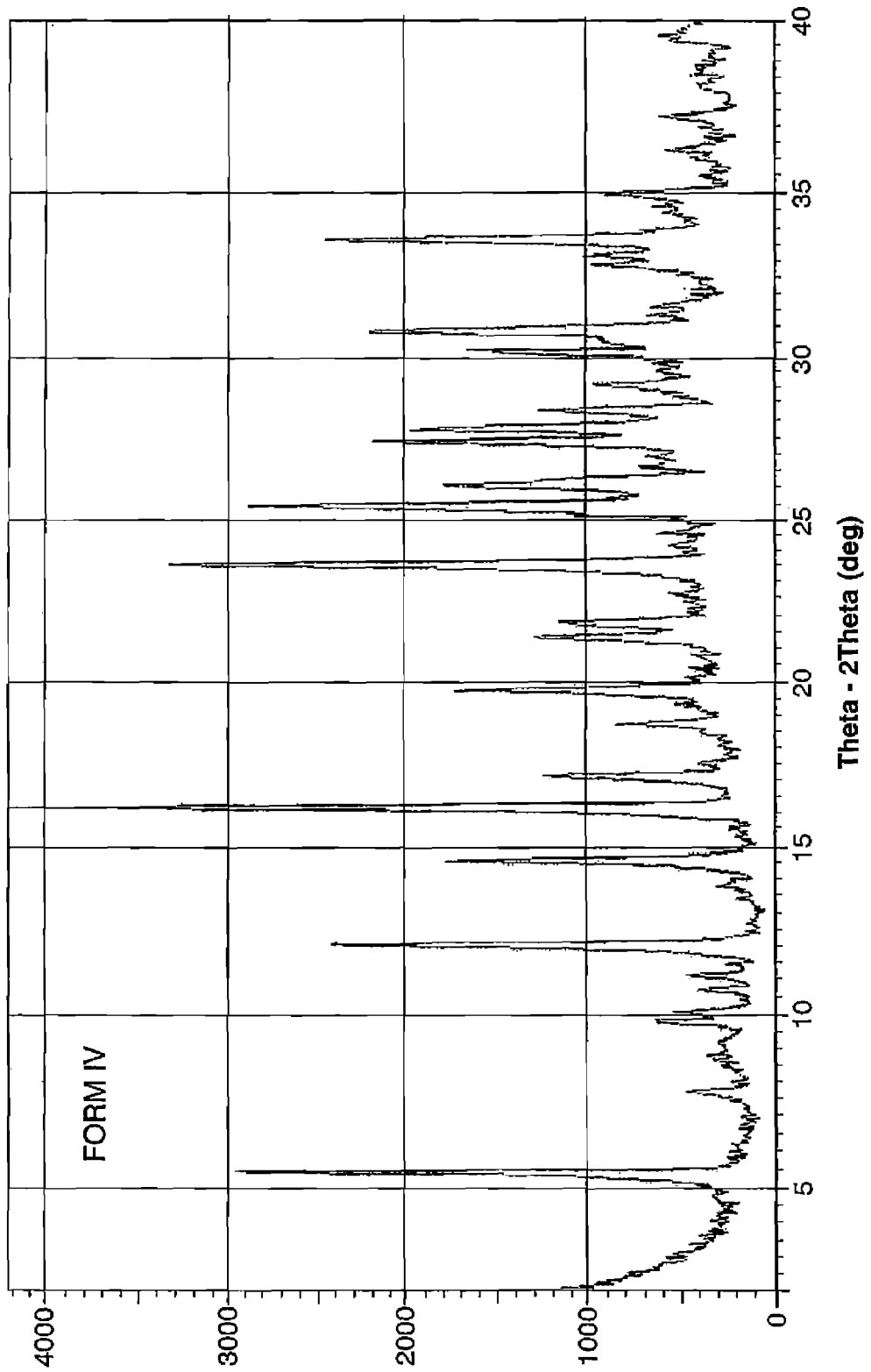

The term "Form IV" as used herein refers to a crystalline polymorph of a pentahydrate of sodium 4-CNAB having an XRPD pattern substantially identical to that shown in FIG. 4. Peak locations (in degrees 2Θ+/−0.2, 0.1, 0.05, or 0.01° 2Θ) for the XRPD pattern in FIG. 4 are provided in Table D below. Form IV exhibits a melting point onset as determined by DSC at about 213.05° C. Form IV converts to Form I upon being heated to about 170-180° C. Form I then begins to melt at about 213.05° C.

TABLE D

| 2-theta | d (Å) |
|---|---|
| 5.47 | 16.13 |
| 6.80 | 12.99 |
| 10.18 | 8.69 |
| 12.24 | 7.23 |
| 13.56 | 6.52 |
| 14.68 | 6.03 |
| 16.29 | 5.44 |
| 16.96 | 5.22 |
| 17.28 | 5.13 |
| 18.27 | 4.85 |
| 19.40 | 4.57 |
| 19.80 | 4.48 |
| 20.36 | 4.36 |
| 21.4 | 1.15 |
| 21.72 | 4.09 |

TABLE D-continued

| 2-theta | d (Å) |
|---|---|
| 23.54 | 3.78 |
| 24.18 | 3.53 |
| 25.96 | 3.43 |
| 26.24 | 3.39 |
| 26.56 | 3.53 |
| 27.26 | 3.27 |
| 27.71 | 3.22 |
| 28.91 | 3.09 |
| 29.40 | 3.04 |
| 29.78 | 3.00 |
| 30.60 | 2.92 |
| 31.80 | 2.81 |
| 32.26 | 2.77 |
| 32.83 | 2.73 |
| 33.32 | 2.69 |
| 34.26 | 2.62 |
| 34.69 | 2.58 |
| 38.41 | 2.34 |
| 39.49 | 2.28 |
| 41.63 | 2.17 |
| 44.61 | 2.03 |
| 44.96 | 2.01 |
| 46.54 | 1.95 |
| 48.56 | 1.87 |

In particular, the peaks (expressed in degrees 2Θ±0.2° 2Θ) at 5.47, 10.2, 16.3, 19.8, 21.7, 23.5, 27.3, 28.9, 30.6, and 33.3 are unique to Form IV.

Form IV may be prepared by exposing Form I, II, III or V of sodium 4-CNAB to a relative humidity of at least about 75% for a time sufficient to yield Form IV of sodium 4-CNAB.

Form V

Figure 5:
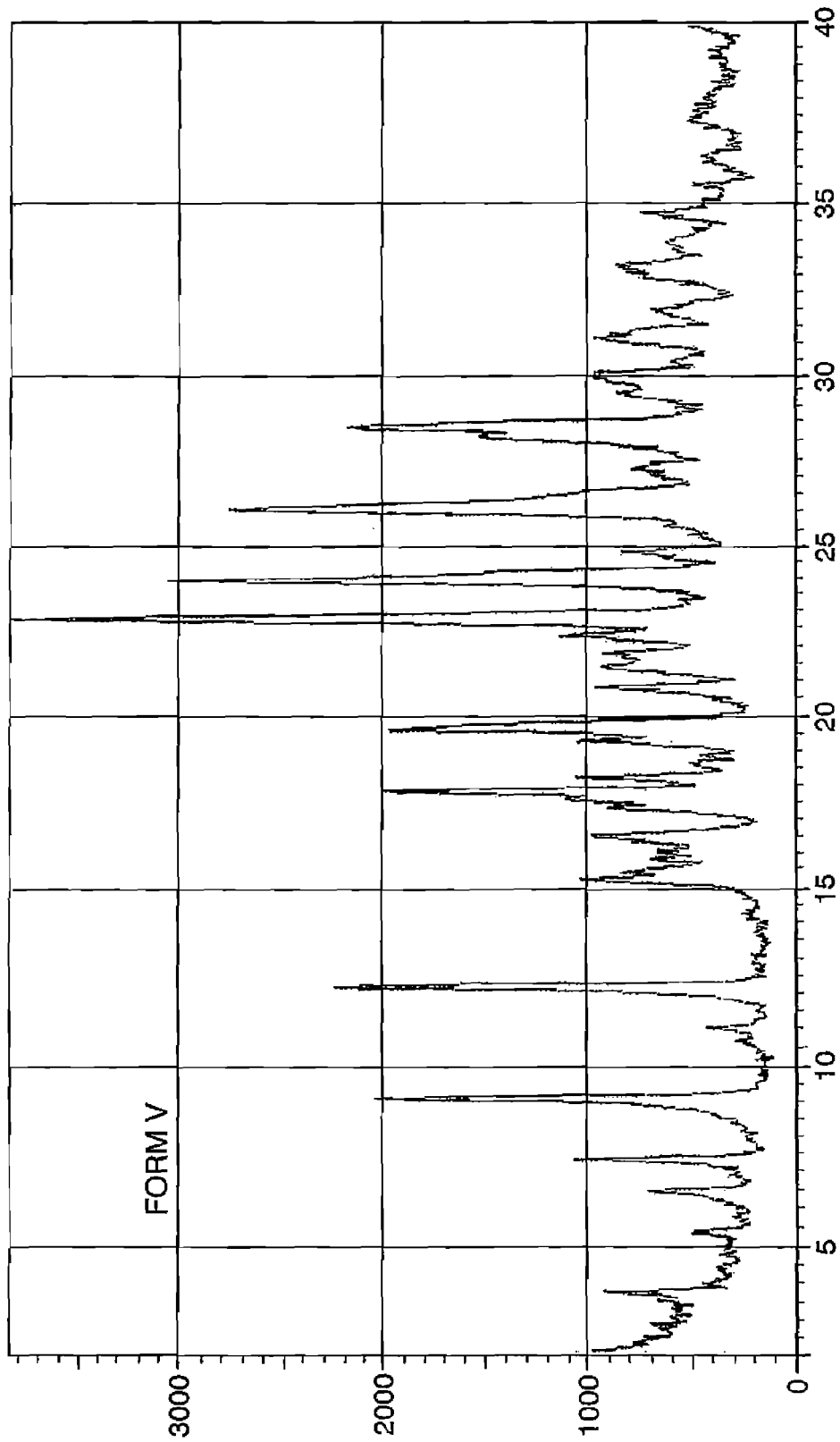

The term "Form V" as used herein refers to an anhydrous crystalline polymorph of sodium 4-CNAB having an XRPD pattern substantially identical to that shown in FIG. 5. Peak locations (in degrees 2Θ±0.2, 0.1, 0.05, or 0.01° 2Θ) for the XRPD pattern in FIG. 5 are provided in Table E below. Form V has a melting point onset as determined by DSC at about 220° C.

TABLE E

| 2-theta | d (Å) |
|---|---|
| 3.68 | 23.98 |
| 5.35 | 16.49 |
| 6.16 | 14.34 |
| 6.50 | 13.67 |
| 7.00 | 12.62 |
| 7.37 | 11.98 |
| 8.64 | 10.23 |
| 9.08 | 9.73 |
| 10.68 | 8.28 |
| 11.09 | 7.97 |
| 11.88 | 7.44 |
| 12.27 | 7.21 |
| 15.28 | 5.79 |
| 15.56 | 5.69 |
| 15.92 | 5.56 |
| 16.12 | 5.49 |
| 16.50 | 5.37 |
| 17.32 | 5.12 |
| 17.79 | 4.98 |
| 18.23 | 4.86 |
| 18.64 | 4.76 |
| 19.32 | 4.59 |
| 19.71 | 4.50 |
| 20.88 | 4.25 |
| 21.44 | 4.14 |
| 21.84 | 4.07 |

TABLE E-continued

| 2-theta | d (Å) |
|---|---|
| 22.38 | 3.97 |
| 22.90 | 3.88 |
| 23.36 | 3.80 |
| 24.04 | 3.70 |
| 24.78 | 3.59 |
| 25.56 | 3.48 |
| 26.09 | 3.41 |
| 26.56 | 3.35 |
| 27.00 | 3.29 |
| 27.28 | 3.27 |
| 27.68 | 3.22 |
| 28.12 | 3.17 |
| 28.44 | 3.14 |

In particular, the peaks (expressed in degrees 2Θ±0.2° 2Θ) at 9.1, 12.3, 17.9, 19.8, 23.0, 24.1, 24.4, 26.1, 28.2, and 28.5 are unique to Form V.

Form V may be prepared by heating Form III of sodium 4-CNAB to a temperature between about 160° C. and the melting point of anhydrous sodium 4-CNAB (e.g., less than about 220° C.) in an environment free of air and water (e.g., a vacuum or nitrogen atmosphere).

Amorphous Form

The amorphous form can be prepared by (1) melting any form of sodium 4-CNAB and solidifying the melt, (2) lyophilization, or (3) recrystallization from an aqueous alcohol solution. Preferably, the molar ratio of alcohol to water in the aqueous alcohol solution is greater than 1 and more preferably greater than 10. A preferred alcohol is isopropanol. A preferred aqueous isopropanol solution has a volume ratio of isopropanol to water of about 19:1.

One or more of the crystalline polymorphs of the present invention can be incorporated into the compositions and delivery systems described herein as delivery agents. According to one embodiment, the composition or delivery system described herein comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of one of Forms I, II, III, IV, and V of sodium 4-CNAB or the amorphous form of sodium 4-CNAB, based upon 100% total weight of 4-CNAB and salts thereof in the composition or delivery system.

According to yet another embodiment, the composition or delivery system described herein comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of one of Forms I, II, III, IV, and V of sodium 4-CNAB or the amorphous form of sodium 4-CNAB, based upon 100% total weight of crystalline 4-CNAB and salts thereof in the composition or delivery system.

According to yet another embodiment, the composition or delivery system described herein comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of one of Forms I, II, III, IV, and V of sodium 4-CNAB, based upon 100% total weight of sodium 4-CNAB in the composition or delivery system.

The composition or delivery system can include one of the crystalline polymorph forms of the present invention and be substantially free or completely free of other crystalline polymorphs of sodium 4-CNAB or one or more of Forms I, II, III, IV, and V of sodium 4-CNAB. For example, the composition can contain Form I, II, III, IV, or V of sodium 4-CNAB in substantially pure form. The terms "substantially free" and "substantially pure" include those compositions and delivery systems that contain less than 0.01, 0.1, 0.2, 0.3, 0.4, 0.5, 1 or 2% by weight of other crystalline polymorphs based upon the total weight of composition or delivery system (or alternatively based upon on the total weight of 4-CNAB and salts thereof or based upon the total weight of crystalline 4-CNAB and salts thereof or based upon the total weight of sodium 4-CNAB) in the composition or delivery system).

The composition or delivery system can include the amorphous of sodium 4-CNAB of the present invention and be substantially free or completely free of other polymorphs of sodium 4-CNAB. For example, the composition can contain the amorphous form of sodium 4-CNAB in substantially pure form. The terms "substantially free" and "substantially pure" include those compositions and delivery systems that contain less than 0.01, 0.1, 0.2, 0.3, 0.4, 0.5, 1 or 2% by weight of other polymorphs based upon the total weight of composition or delivery system (or alternatively based upon on the total weight of 4-CNAB and salts thereof or based upon the total weight of crystalline 4-CNAB and salts thereof or based upon the total weight of sodium 4-CNAB) in the composition or delivery system).

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of muco-polysaccharides; carbohydrates; lipids; other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof. Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including $\alpha$, $\beta$ and $\gamma$; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof. Other suitable forms of insulin, including, but not limited to, synthetic forms of insulin, are described in U.S. Pat. Nos. 4,421,685, 5,474,978, and 5,534,488, each of which is hereby incorporated by reference in its entirety.

Delivery Systems

The compositions of the present invention comprise (a) one or more of Forms I, II, III, and IV, and V of sodium 4-CNAB or the amorphous form of sodium 4-CNAB and (b) one or more active agents. In one embodiment, the delivery agent is mixed with the active agent prior to administration.

The administration compositions may be in the form of a liquid. Such liquids typically include a dosing vehicle. The dosing vehicle may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycols, sorbitol, maltitol, and sucrose. Dosing solutions may be prepared by mixing a solution of the delivery agent compound with a solution of the active agent, just prior to administration. Alternately, a solution of the delivery agent (or active agent) may be mixed with the solid form of the active agent (or delivery agent). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze drying, precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions may deliver active agents more efficiently than prior compositions, lower amounts of biologically or chemically active agents than those used in prior dosage unit forms or delivery systems can be administered to the subject, while still achieving the same blood levels and/or therapeutic effects.

The presently disclosed compounds deliver biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

Insulin/Sodium 4-CNAB Pharmaceutical Compositions

Pharmaceutical compositions containing insulin and one or more polymorphs of the present invention or the amorphous form of sodium 4-CNAB may be prepared with adjuvants, diluents, and excipients as known in the art, including those described above and in *Remington's Pharmaceutical Sciences*, Joseph P. Remington, 17$^{th}$ Ed., Mack Pub. Co. (1985), which is hereby incorporated by reference. Suitable excipients include isotonic agents, preservatives and buffers. Non-limiting examples of isotonic agents are sodium chloride, mannitol and glycerol. Non-limiting examples of preservatives are phenol, m-cresol, methyl p-hydroxybenzoate and benzyl alcohol. Non-limiting examples of suitable buffers are sodium acetate and sodium phosphate.

The pharmaceutical compositions may be prepared by mixing the sodium 4-CNAB, insulin, and other ingredients in dry or liquid form. Dosage forms, such as tablets and capsules, may be prepared from such mixtures by methods known in the art.

The insulin pharmaceutical composition of the present invention may be formulated into a dosage unit form as discussed above.

The insulin compositions of this invention can be used in the treatment of diabetes. The optimal dose level for any patient will depend on a variety of factors including the efficacy of the specific human insulin derivative employed, the age, body weight, physical activity, and diet of the patient, on a possible combination with other drugs, and on the severity of the case of diabetes.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired. The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

DSC

The melting points cited were determined by differential scanning calorimety (DSC). The quoted values were obtained with Perkin Elmer Pyris 1 software for Windows. The instrument was calibrated for temperature using the melting points of irdium and zinc, and for enthalpy using the enthalpy of fusion of indium. Calibration checks were performed on a routine basis using an indium standard. Samples were sealed in an aluminum pan with a crimped lid that had a tiny hole in it. The samples were then heated in a nitrogen atmosphere from 30 to 250° C. at 10° C./min. Un-milled samples were lightly ground with a mortar and pestle prior to analysis in order to improve thermal contact with the surfaces of the sample pan.

XRPD

The Powder X-Ray diffraction analysis was done using a Shimadzu XRD-6000 powder diffractometer, available from Shimadzu Scientific Instruments, Inc. of Columbia, Md. The instrument was calibrated using silicon powder, and the calibration was found to be correct when it was tested with an NIST #675 low-angle diffraction standard. The samples were illuminated with Cu Kα radiation ($\lambda$=1.54056 Å). Un-milled samples were lightly ground with a mortar and pestle so that a sample could be prepared for analysis with a smooth, even, surface. The diffraction pattern between 2 and 40° 2θ was used as a fingerprint region to identify the crystal structure present in the lots.

Thermogravimetric Analysis (TGA)

Thermogravimetric analysis of sodium 4-CNAB was conducted using a Perkin-Elmer TGA7 thermogravimetric analyzer with Pyris 1 for Windows software. The instrument was calibrated for temperature using the curie points of alumel and tin. Samples were heated in a nitrogen atmosphere from 30 to 300° C. and the percent change in weight as a function of temperature was recorded. The un-milled lots were lightly ground with a mortar and pestle prior to analysis in order to improve contact with the inner surfaces of the platinum sample holder.

Water Sorption-Desorption Behavior

Sorption analysis was conducted using an SGA-100 Symmetric Vapor Sorption Analyzer (available from VTI Corporation of Hialeah, Fla.). The instrument was calibrated using PVP and NaCl. Samples were dried to constant weight at 60° C. prior to analysis. The equilibrium water content of the sample from 5% relative humidity (RH) to 95% RH and then back down to 5% RH was determined at 25° C.

FTIR

FTIR was performed on a Perkin Elmer Spectrum BX FT-IR using KBr discs. 1 mg of sample was dispersed in 150 mg KBr. The resolution was 4 cm$^{-1}$ and 32 scans were averaged.

EXAMPLE 1

Compound Preparation

1a. Preparation of the Free Acid of 4-CNAB

4-Chlorosalicylic acid (10.0 g, 0.0579 mol) was added to a one-neck 250 ml round-bottomed flask containing about 50 ml methylene chloride. Stirring was begun and continued for the remainder of the reaction. Coupling agent 1,1-carbonyldiimidazole (9.39 g, 0.0579 mol) was added as a solid in portions to the flask. The reaction was stirred at room temperature for approximately 20 minutes after all of the coupling agent had been added and then ethyl-4-aminobutyrate hydrochloride (9.7 g, 0.0579 mol) was added to the flask with stirring. Triethylamine (10.49 ml, 0.0752 mol) was added dropwise from an addition funnel. The addition funnel was rinsed with methylene chloride. The reaction was allowed to stir at room temperature overnight.

The reaction was poured into a separatory funnel and washed with 2N HCl and an emulsion formed. The emulsion was left standing for two days. The emulsion was then filtered through celite in a fritted glass funnel. The filtrate was put back in a separatory funnel to separate the layers. The organic layer was dried over sodium sulfate, which was then filtered off and the filtrate concentrated by rotary evaporation. The resulting solid material was hydrolyzed with 2N NaOH, stored overnight under refrigeration, and then hydrolyzing resumed. The solution was acidified with 2N HCl and the solids that formed were isolated, dried under vacuum, and recrystallized twice using methanol/water. Solids precipitated out overnight and were isolated and dried. The solids were dissolved in 2N NaOH and the pH of the sample was brought to pH 5 with 2N HCl. The solids were collected and HPLC revealed a single peak. These solids were then recrystallized in methanol/water, isolated, and then dried under vacuum, yielding 4.96 g (33.0%) of 4-(4 chloro-2-hydroxybenzoyl)aminobutyric acid. ($C_{11}H_{12}ClNO_4$; Molecular weight 257.67.) Melting point: 131-133° C. Combustion analysis: % C, 51.27 (calc.), 51.27 (found); % H, 4.69 (calc.), 4.55 (found); % N: 5.44 (calc.), 5.30 (found). H NMR Analysis: ($d_6$-DMSO): δ 13.0, s, 1H(COOH); δ 12.1, s, 1H(OH); δ 8.9, t, 1H(NH); δ 7.86, d, 1H (H ortho to amide); δ 6.98, d, 1H(H ortho to phenol OH); δ 6.96, d, 1H, (H meta to amide); δ 3.33, m, 2H($CH_2$ adjacent to NH); δ 2.28, t, 2H($CH_2$ adjacent to COOH); δ 1.80, m, 2H (aliphatic $CH_2$ beta to NH and $CH_2$ beta to COOH).

1b. Additional Preparation of the Free Acid of 4-CNAB

4-Chlorosalicylic acid (25.0 g, 0.1448 mol) was added to a one-neck 250 ml round-bottomed flask containing about 75-100 ml methylene chloride. Stirring was begun and continued to the remainder of the reaction. Coupling agent 1,1-carbonyldiimidazole (23.5 g, 0.1448 mol) was added as a solid in portions to the flask. The reaction was stirred at room temperature for approximately 20 minutes after all of the coupling agent had been added and then ethyl-4-aminobutyrate hydrochloride (24.3 g 0.1448 mol) was added to the flask with stirring. Triethylamine (26.0 ml, 0.18824 mol) was added dropwise from an addition funnel. The addition funnel was rinsed with methylene chloride. The reaction was allowed to stir at room temperature overnight.

The reaction was poured into a separatory funnel and washed with 2N HCl and an emulsion formed. The emulsion was filtered through celite in a fritted glass funnel. The filtrate was put back in a separatory funnel to separate the layers. The organic layer was washed with water and brine, then dried over sodium sulfate, which was then filtered off and the filtrate concentrated by rotary evaporation. The resulting solid material was hydrolyzed with 2N NaOH overnight. The solution was acidified with 2N HCl and the brown solids that formed were recrystallized using methanol/water, hot filtering off insoluble black material. White solids precipitated out and were isolated and dried, yielding 11.68 g (37.0%) of 4-(4 chloro-2-hydroxybenzoyl)aminobutyric acid. ($C_{11}H_{12}CNO_4$; Molecular weight 257.67.) Melting point: 129-133° C. Combustion analysis: % C, 51.27 (calc.), 51.26 (found); % H, 4.69 (calc.), 4.75 (found); % N: 5.44 (calc.), 5.32 (found). H NMR Analysis: ($d_6$-DMSO): δ 13.0, s, 1H(COOH); δ 12.1, s, 1H(OH); δ 8.9, t, 1H(NH); δ 7.86, d, 1H (H ortho to amide); δ 6.98, d, 1H(H ortho to phenol OH); δ 6.96, d, 1H, (H meta to amide); δ 3.33, m, 2H($CH_2$ adjacent to NH); δ 2.28, t, 2H($CH_2$ adjacent to COOH); δ 1.80, m, 2H (aliphatic $CH_2$ beta to NH and $CH_2$ beta to COOH).

1c. Additional Preparation of the Free Acid of 4-CNAB

A 22 L, five neck, round bottom flask was equipped with an overhead stirrer, 1 L Dean-Stark trap with reflux condenser, thermocouple temperature read out, and heating mantle. The following reaction was run under a dry nitrogen atmosphere. Reagent n-butanol (5000 mL) and 4-chlorosalicylic acid (2000 g, 11.59 mol) were charged to the reaction flask. The Dean-Stark trap was filled with n-butanol (1000 mL). Concentrated sulfuric acid (50 g) was added. The reaction mixture was heated to reflux for approximately 120 hours. Approximately 206 mL water was collected in the trap during this time. The heating mantle was removed and the reaction mixture allowed to cool to ambient temperature. The Dean-Stark trap was drained and removed. Deionized water (1000 mL) was charged. The biphasic mixture was stirred for 10 minutes. Stirring was stopped and the phases allowed to separate. The lower aqueous phase was siphoned off and discarded. A 10 wt % aqueous solution of sodium bicarbonate (1000 mL) was charged to the reaction mixture. The mixture was stirred for 10 minutes. The reaction mixture was tested with pH paper to ensure the pH of the solution was greater than 7. Water (500 mL) was added to the reaction mixture. The stirring was stopped and the phases allowed to separate. The lower aqueous layer was siphoned off and discarded. The reaction mixture was washed with another 500 mL portion of deionized water. The reactor was set up for atmospheric distillation into a tared 5 L receiver. The mixture was distilled until the pot temperature rose to between 140 and 150° C. The distillation was switched from atmospheric distillation to vacuum distillation. The pressure in the distillation setup was slowly lowered to 100 mmHg. The pot temperature fell and the remaining n-butanol and n-butyl ether (a reaction byproduct) distilled off. The heating was stopped and the reaction mixture allowed to cool to ambient temperature. The vacuum was broken with dry nitrogen. The crude butyl ester was transferred to a 5 L pot flask of a vacuum distillation setup. The crude butyl ester was distilled at a pressure between 0.2 and 0.5 mmHg. The forerun collected at a head temperature of <40° C. was discarded. The butyl 4-chloro-2-hydroxybenzoate fraction was collected at a head temperature between 104 and 112° C. This fraction had a weight of 2559 g. The yield was 96%.

A 22 L, five neck, round bottom flask was equipped with an overhead stirrer, reflux condenser, thermocouple temperature read out, and a heating mantle. The reactor was purged with nitrogen. Butyl 4-chloro-2-hydroxybenzoate (2559 g, 11.2 moles) and reagent methanol (10,000 mL) were charged to the reaction flask, and the contents were stirred until a solution was obtained. The reaction mixture was filtered through a Buchner funnel and returned to the reactor. The stirring rate was increased, and gaseous ammonia was added rapidly to the headspace of the reactor. The ammonia gas addition was continued until the temperature of the reactor reached 45° C. The addition of the ammonia was suspended and the agitation rate lowered. The reaction was allowed to cool to ambient temperature. Ammonia gas addition, as described above, was repeated until the reaction was complete as indicated by liquid chromatography. Seven ammonia charges over five days were needed to complete the reaction. Approximately half of the solvent was removed by atmospheric distillation. The reaction mixture was cooled to ambient temperature and 5 L of deionized water was added. Concentrated hydrochloric acid (approximately 500 mL) was added slowly to the reactor until the pH of the reaction mixture was between 4 and 5. The resulting precipitate was collected by vacuum filtration through a large sintered glass funnel. The product filter cake was washed with 2000 mL of deionized water, and dried at 50° C. for 32 hours to give 1797 g of 4-chloro-2-hydroxybenzamide. The yield was 94%.

A 22 L, five neck, round bottom flask was equipped with an overhead stirrer, reflux condenser, addition funnel, thermocouple temperature read out, and a heating mantle. The reactor was purged with nitrogen. Acetonitrile (4700 mL) and 4-chloro-2-hydroxybenzamide (1782 g, 10.4 mol) were charged to the reaction flask and the stirring was started. Pyridine (1133 mL, 14.0 mol) was charged to the reactor. The resulting reaction slurry was cooled to less than 10° C. with an ice bath. Ethyl chloroformate (1091 mL, 1237 g, 11.4 mol) was placed in the addition funnel and charged slowly to the stirred reaction mixture such that the temperature of the reaction mixture did not exceed 15° C. during the addition. The temperature of the reaction mixture was held between 10 and 15° C. for 30 minutes after the ethyl chloroformate addition was complete. The ice bath was removed, and the reaction mixture was warmed to ambient temperature. The reaction mixture was then slowly heated to reflux and held at that temperature for 18 hours. Liquid chromatographic analysis of the reaction mixture indicated that the reaction was only 80% complete. Approximately half of the solvent was removed by atmospheric distillation. The reaction mixture was cooled first to ambient temperature and then to <10° C. with an ice bath. Additional pyridine (215 mL, 2.65 mol) was added to the reaction mixture. Ethyl chloroformate (235 g, 2.17 mol) was added slowly via an addition funnel to the cold reaction mixture. The reaction mixture was held between 10 and 15° C. for 30 minutes after the ethyl chloroformate addition was complete. The ice bath was removed, and the reaction mixture was warmed to ambient temperature. The reaction mixture was then slowly heated to reflux and held at that temperature for 18 hours, after which time liquid chromatographic analysis indicated that the reaction was complete. The reaction mixture was cooled first to ambient temperature and then to <10° C. with an ice bath. Water (1600 mL) was added slowly via an addition funnel and the resulting slurry held at <10° C. for 90 minutes. The solid product was collected by vacuum filtration through a large sintered glass funnel. The product filter cake was washed with deionized water and vacuum dried at 50° C. for 18 hours to give 1914 g of 7-chloro-2H-1,3-benzoxazine-2,4(3H)-dione as a tan solid. The yield was 83%.

A 22 L, five neck, round bottom flask was equipped with an overhead stirrer, reflux condenser, thermocouple temperature read out, and heating mantle. The following reaction was run under a dry nitrogen atmosphere. 7-Chloro-2H-1,3-benzoxazine-2,4(3H)-dione (1904 g, 9.64 mol), ethyl 4-bromobutyrate (1313 mL, 9.18 mol), and N,N-dimethylacetamide (4700 mL) were charged under a nitrogen purge. The reaction mixture was heated to 70° C. Sodium carbonate (1119 g, 10.55 mol) was charged to the clear solution in five equal portions over approximately 40 minutes. The reaction mixture was held at 70° C. overnight. The reaction was cooled to 55° C. The inorganic solids were removed by vacuum filtration through a sintered glass funnel. The reaction flask was rinsed with 2B-ethanol (2000 mL) and this rinse used to wash the filter cake. The reaction flask was cleaned with deionized water. The filtrate was returned to the clean reaction flask. The filtrate was cooled in an ice bath. Deionized water (9400 mL) was added slowly with an addition funnel. The chilled mixture was allowed to stir overnight. The resulting solids were recovered by vacuum filtration through a sintered glass funnel. The product cake was washed with deionized water. The ethyl 3-(4-butanoate)-7-chloro-2H-1,3-benzoxazine-2,4-(3H)-dione had a weight of 2476.0 g. The yield was 82.2%.

A 12 L, stainless steel reactor was equipped with an overhead stirrer, reflux condenser, thermocouple temperature read out, addition funnel, and heating mantle. The following reaction was run under a dry nitrogen atmosphere. Water (3 L) and ethyl 3-(4-butanoate)-7-chloro-2H-1,3-benzoxazine-2,4-(3H)-dione (1118 g, 3.58 mol) were charged to the reactor and stirring was started. A solution of sodium hydroxide (574 g, 14.34 mol) in water (2 L) was added slowly to the reaction slurry. The reaction was heated to 70° C. for 6 hours, and then allowed to cool slowly to ambient temperature. The reaction mixture was filtered through a Buchner funnel. A 22 L five neck round bottom flask was equipped with an overhead stirrer, reflux condenser, thermocouple temperature read out, and an addition funnel. Deionized water (1880 mL) and concentrated hydrochloric acid (1197 g, 12.04 mol) were charged to the reactor. The hydrolysate from above was added slowly via addition funnel to the acid solution. The pH of the resulting slurry was adjusted to 3 by adding additional hydrochloric acid (160 mL, 1.61 mol). The product solids were collected by filtration through a sintered glass funnel and dried in a vacuum oven at 50° C. for 24 hours to give 1109.3 g of 4-[(4-chloro-2-hydroxy-benzoyl)amino]butanoic acid as an off white solid. The yield was quantitative.

EXAMPLE 1d

Preparation of Form I(Anhydrous Sodium 4-CNAB)

Figure 6:
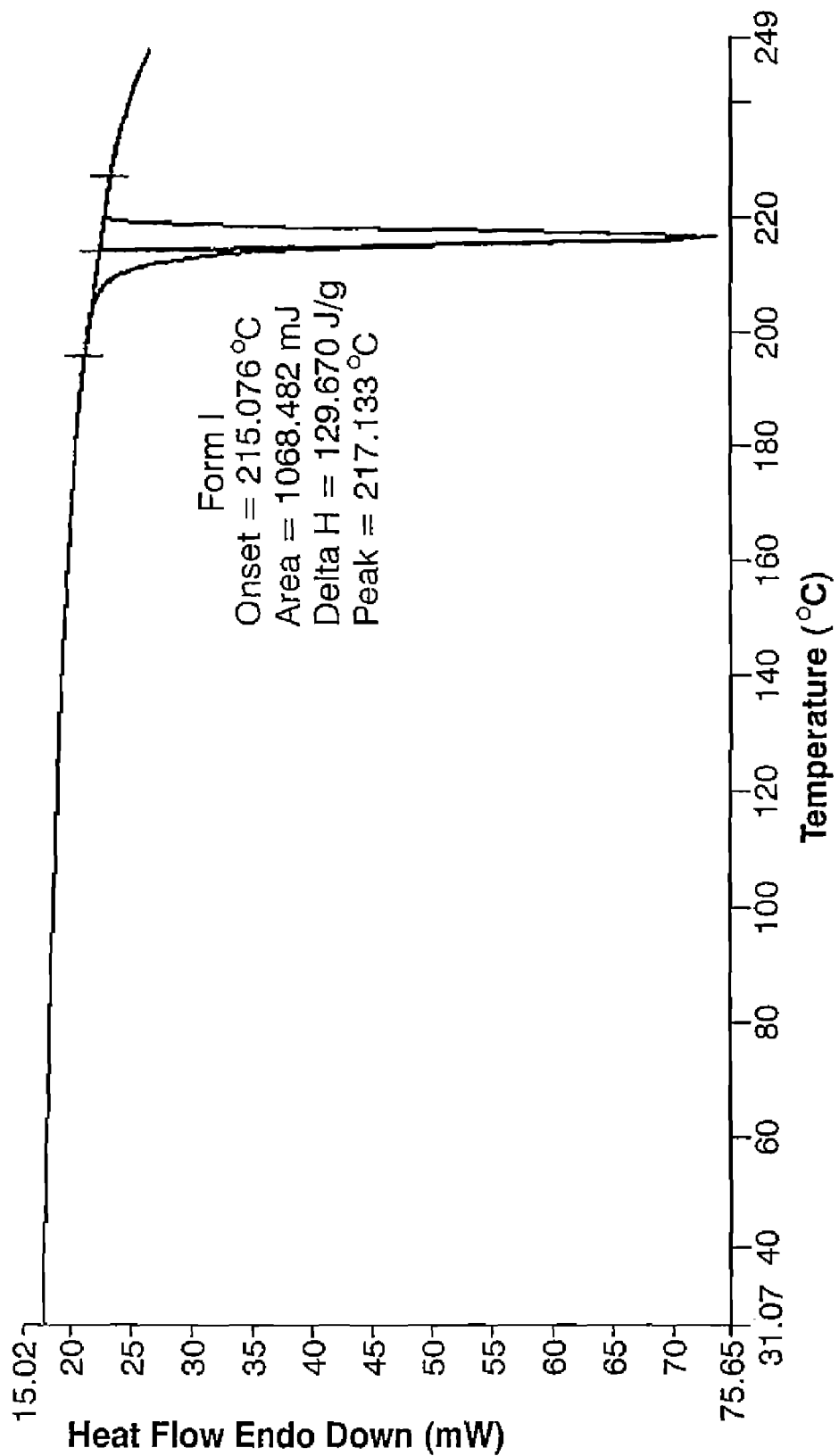
FIGS. 6-10 are differential scanning calorimety (DSC) scans of Forms I-V of sodium 4-CNAB, respectively.
Figure 7:
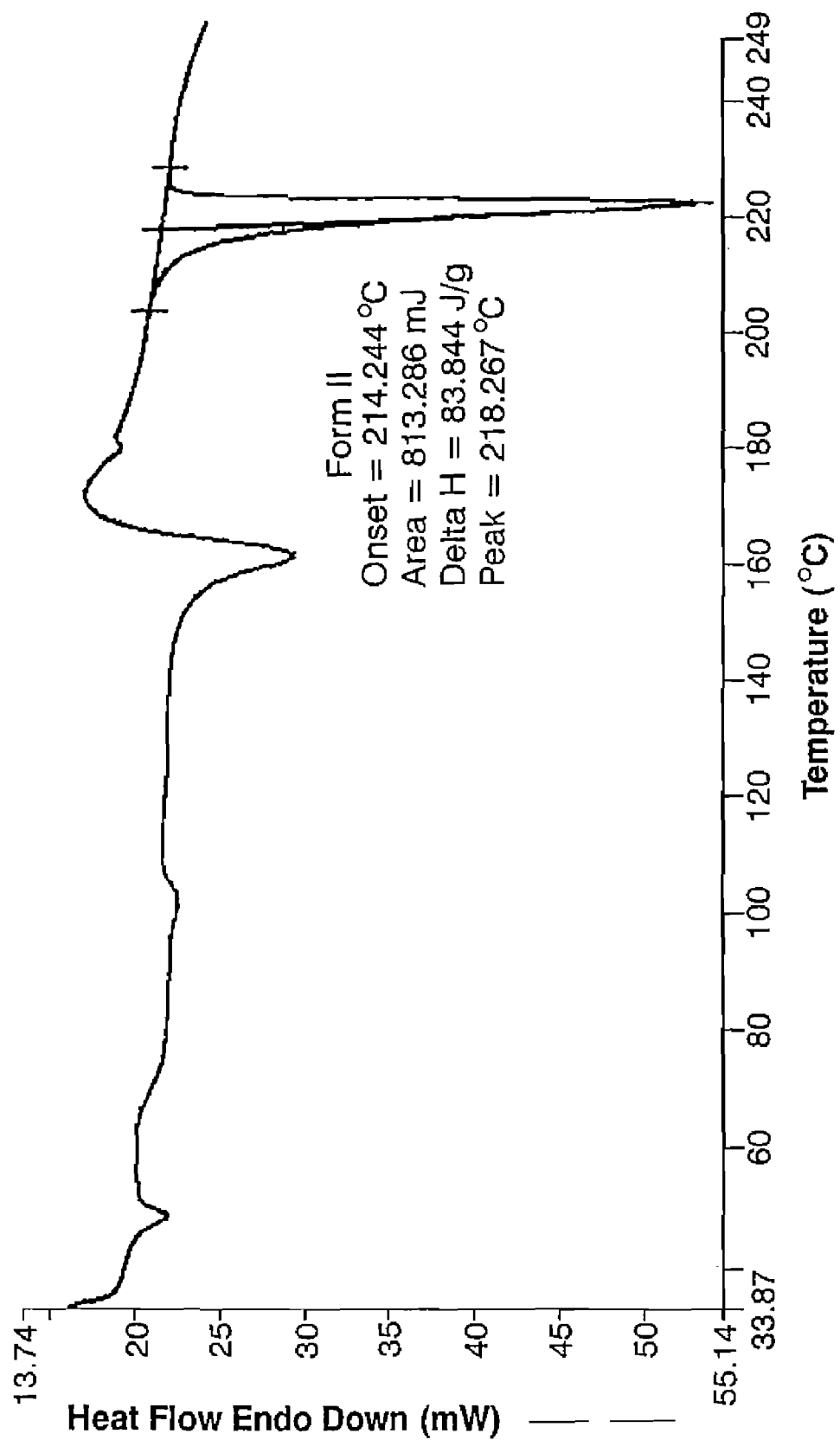
Figure 8:
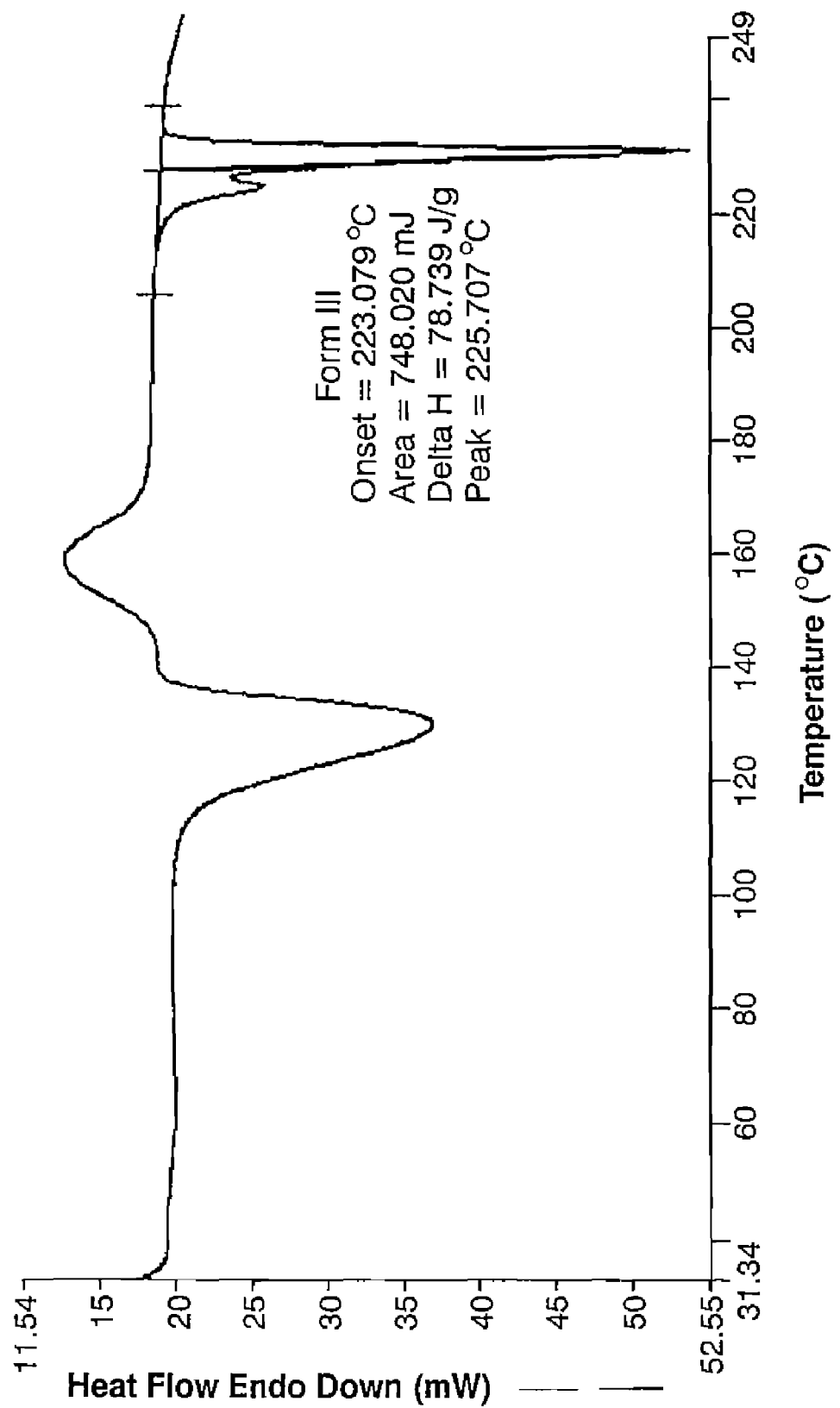
Figure 11:
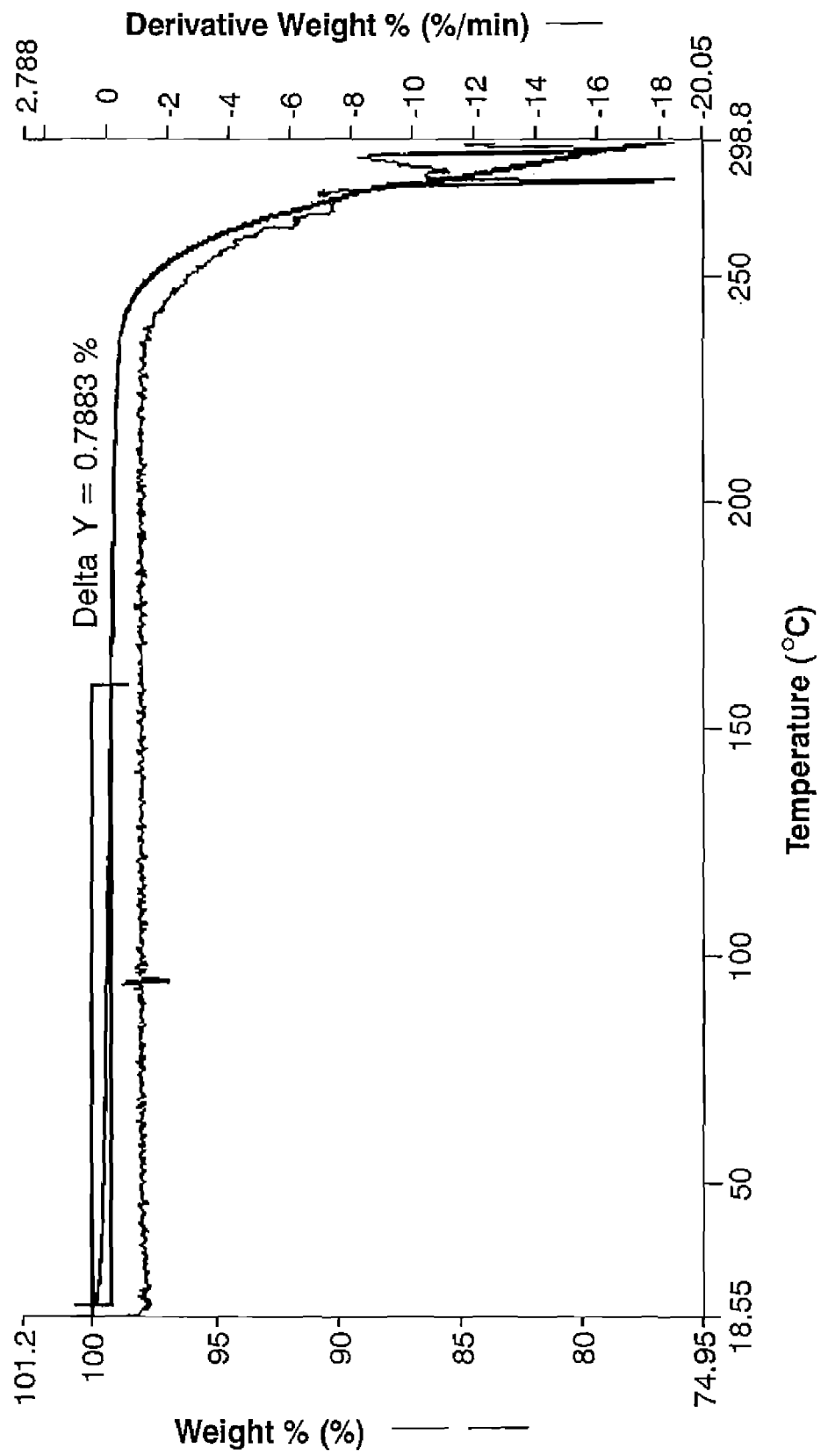
FIG. 11 is a thermogravimetric analysis (TGA) of Form I of sodium 4-CNAB.
Figure 12A:
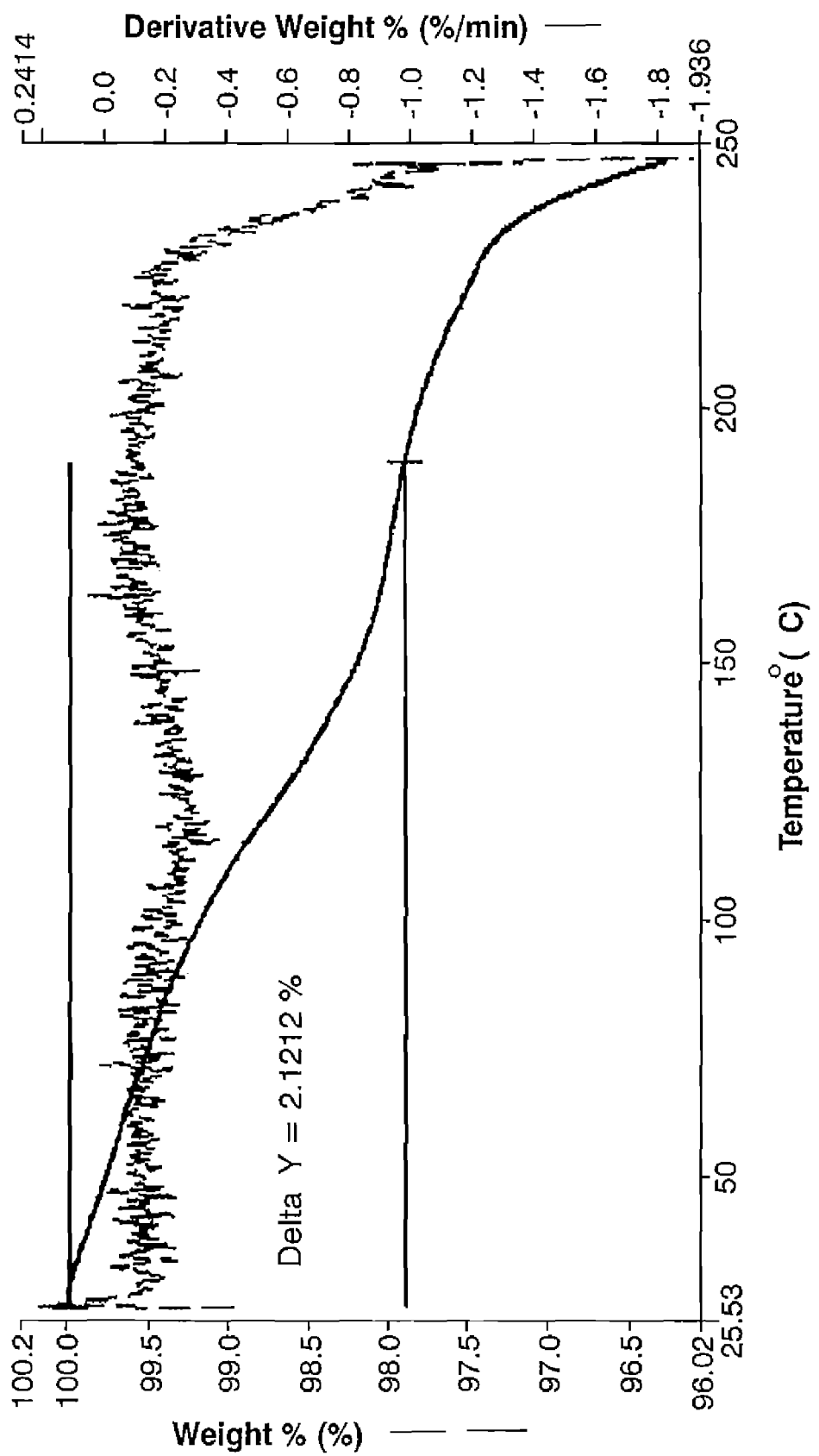
FIGS. 12A and 12B are TGAs of Form II of sodium 4-CNAB.
Figure 12B:
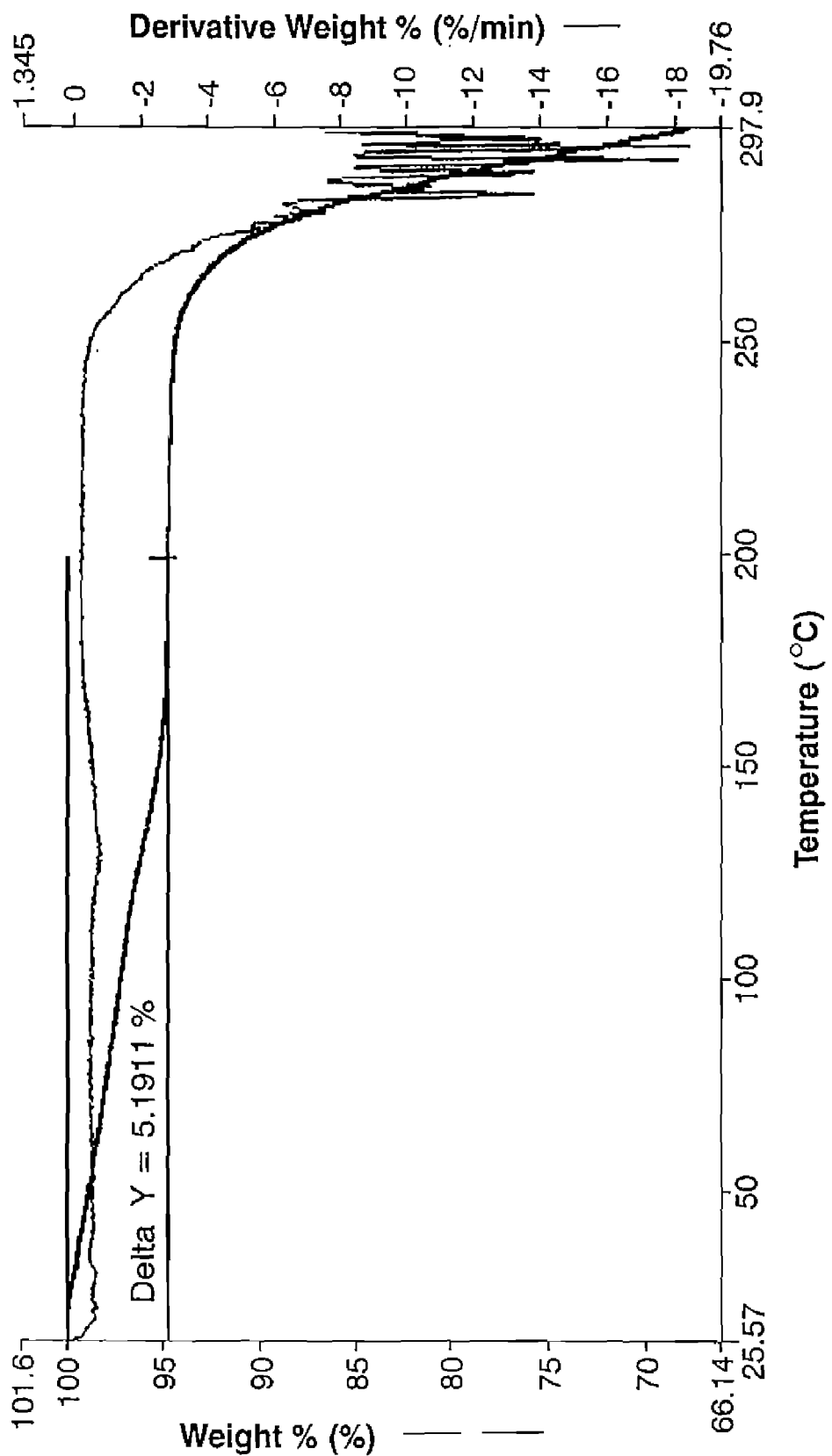
Figure 13:
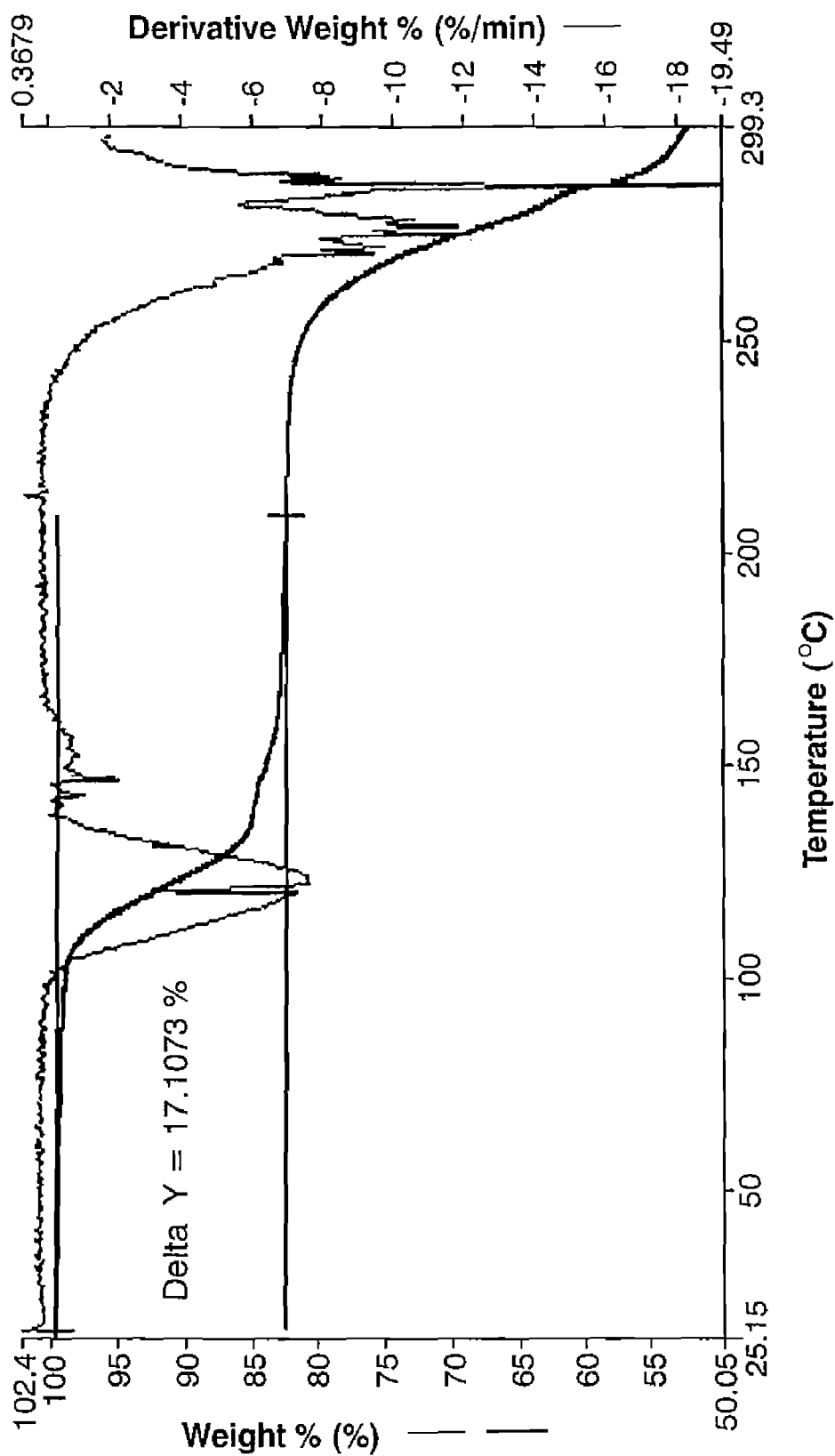
FIGS. 13-15 are TGAs of Forms III-V of sodium 4-CNAB, respectively.
Figure 16A:
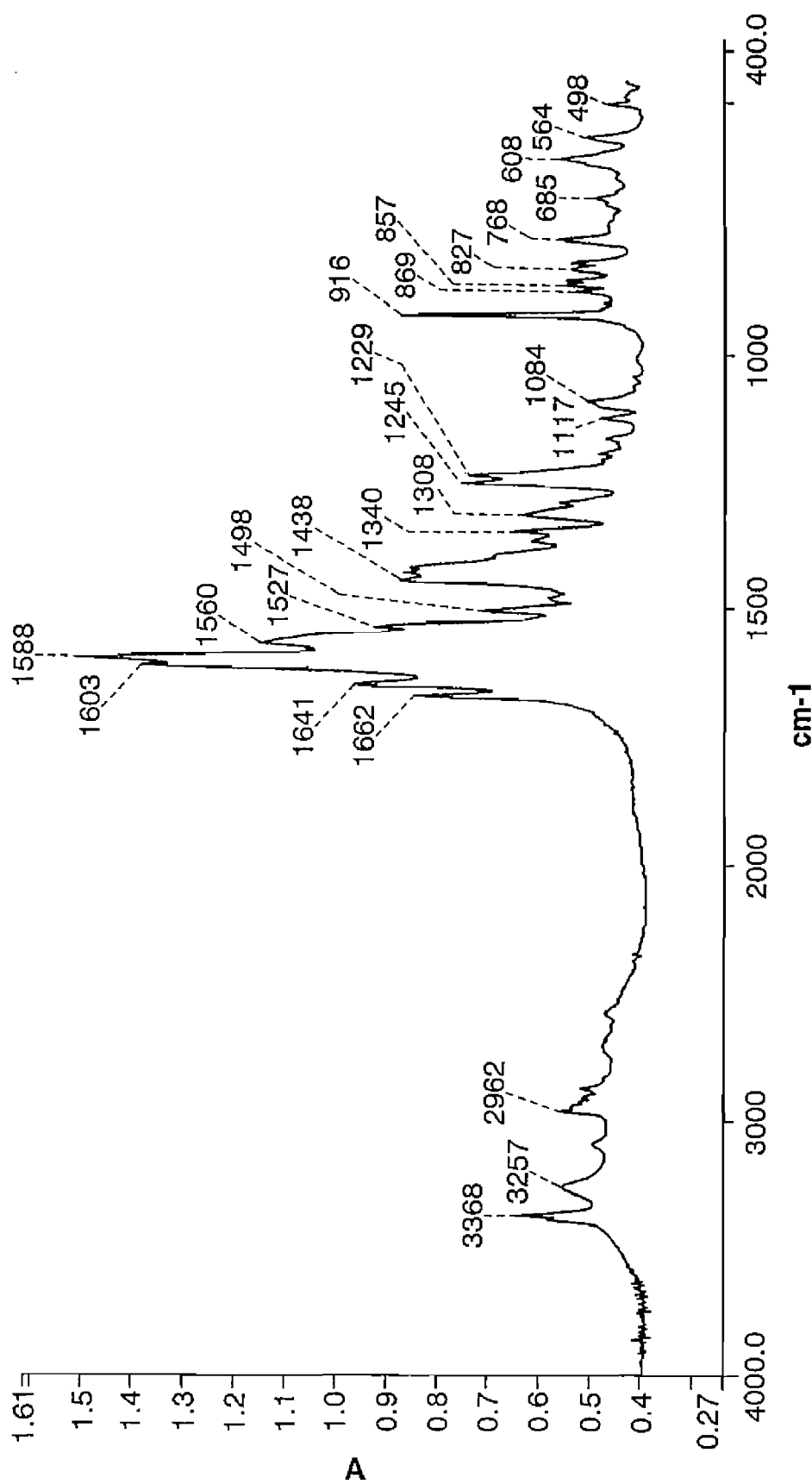
FIGS. 16A and 16B are FTIR spectra of Form I of sodium 4-CNAB.
Figure 16B:
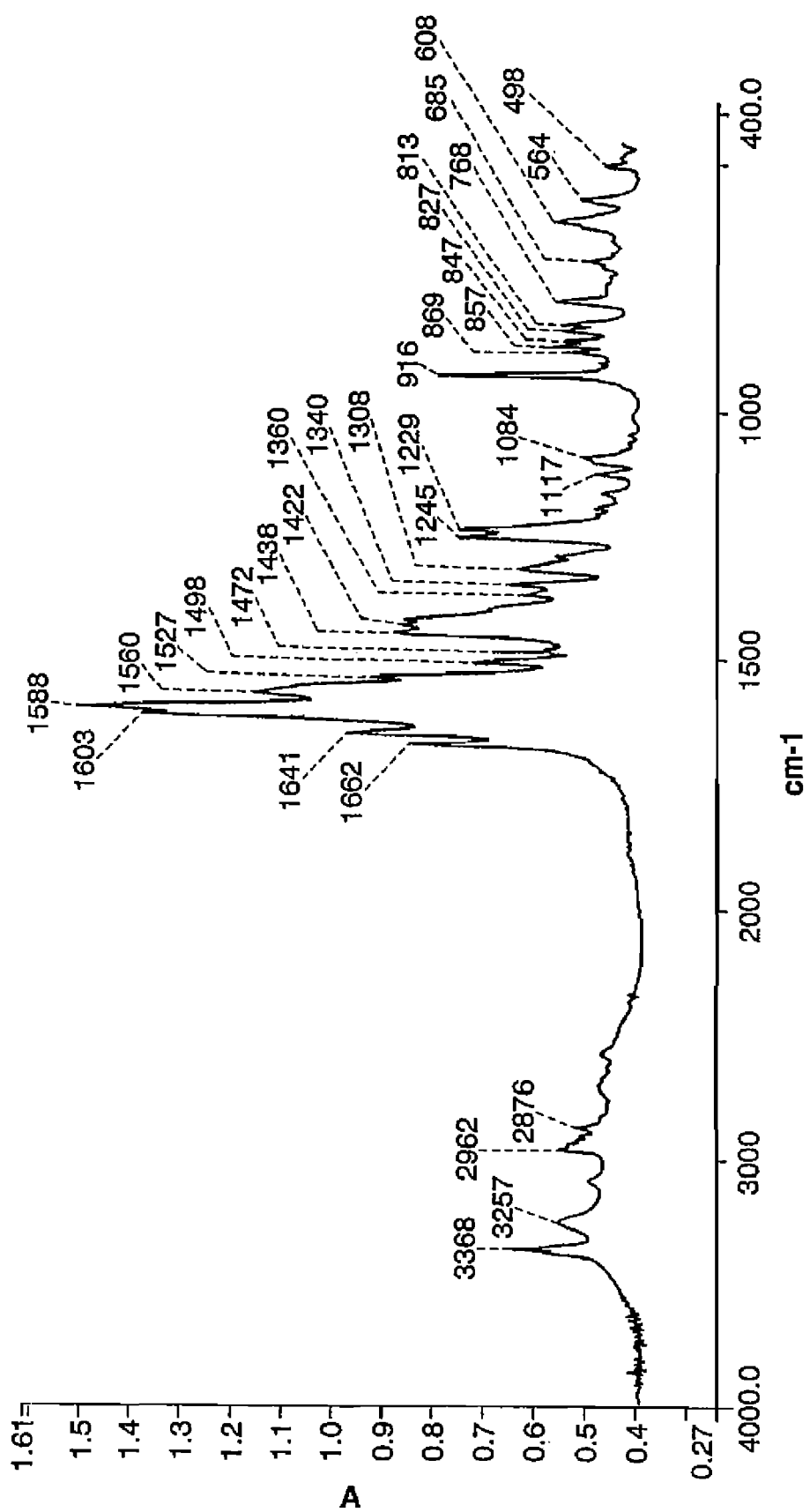
Figure 17:
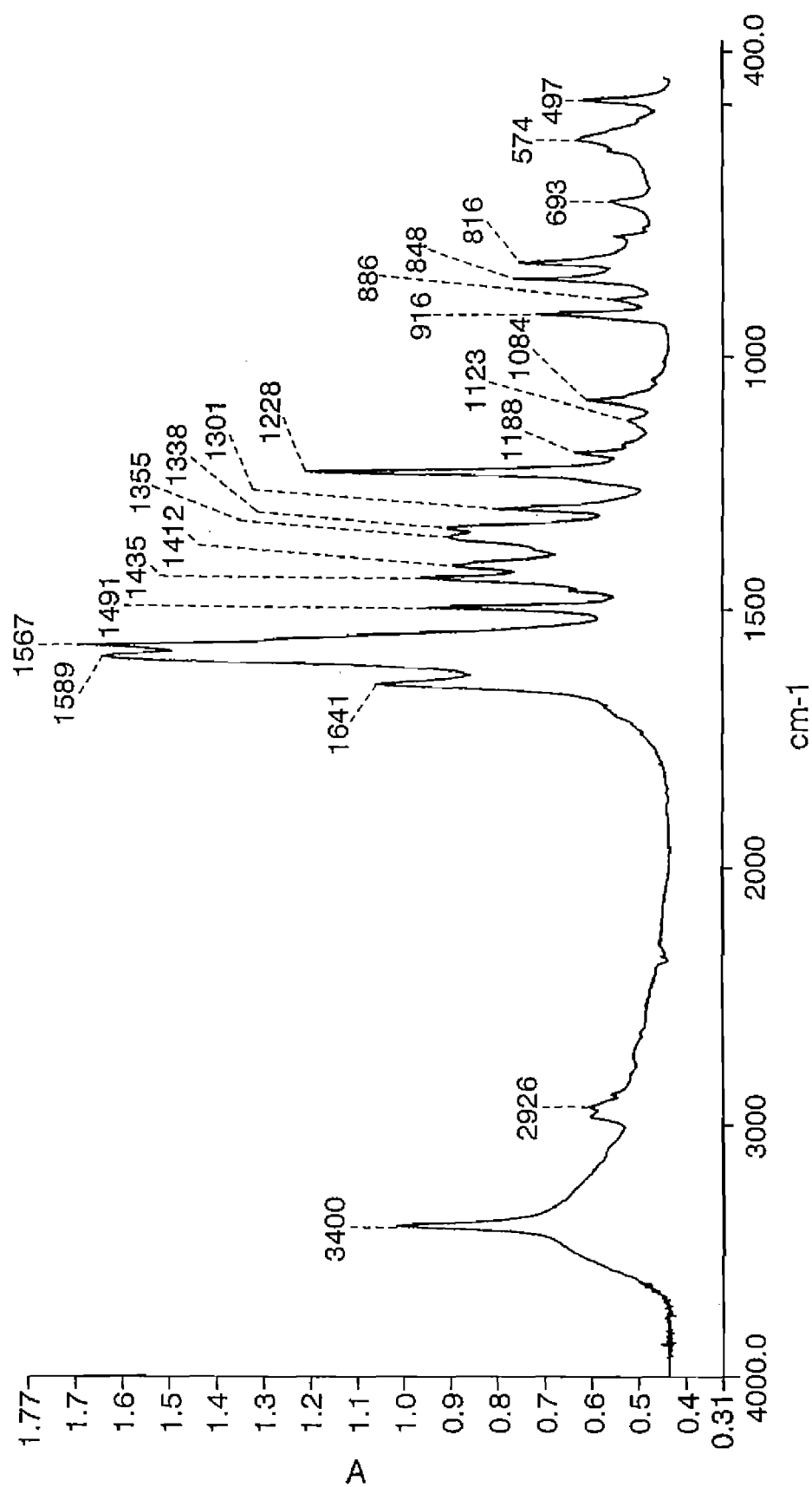
FIGS. 17-20 are an FTIR spectra of Forms II-V of sodium 4-CNAB, respectively.
Figure 18:
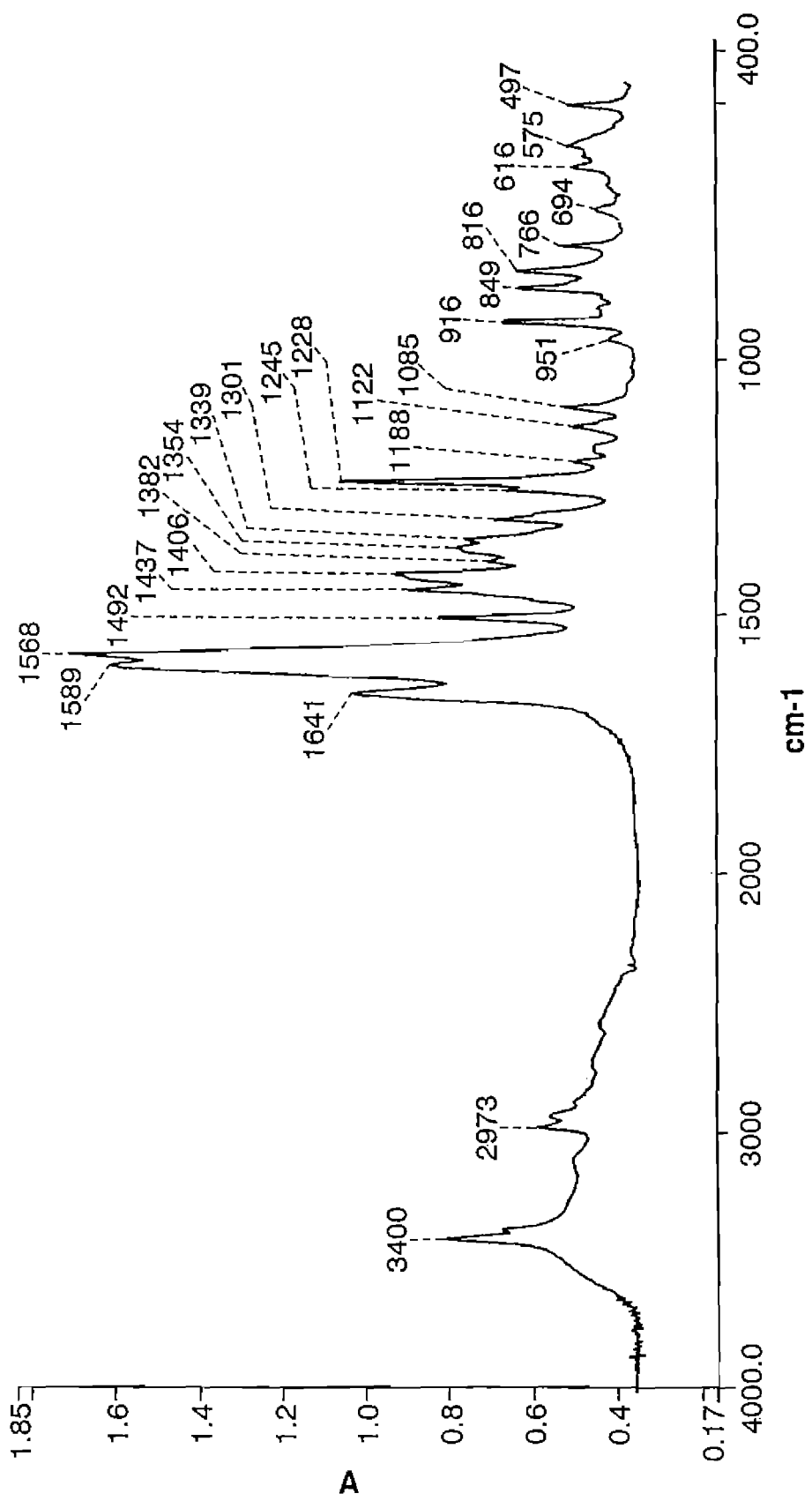
Figure 22:
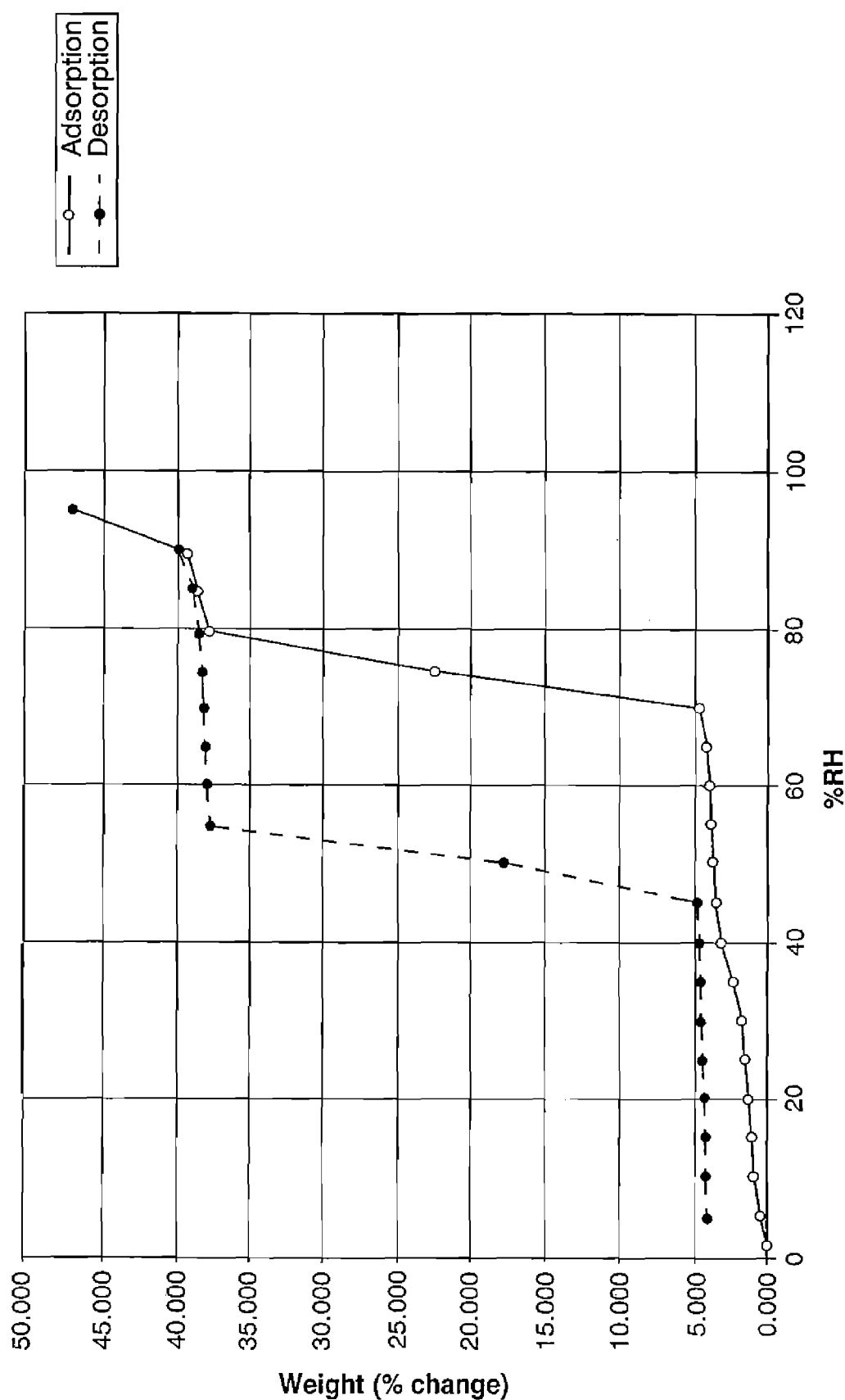
FIGS. 22-25 are moisture adsorption/desorption curves for Forms I-III and V of sodium 4-CNAB, respectively.
Figure 23:
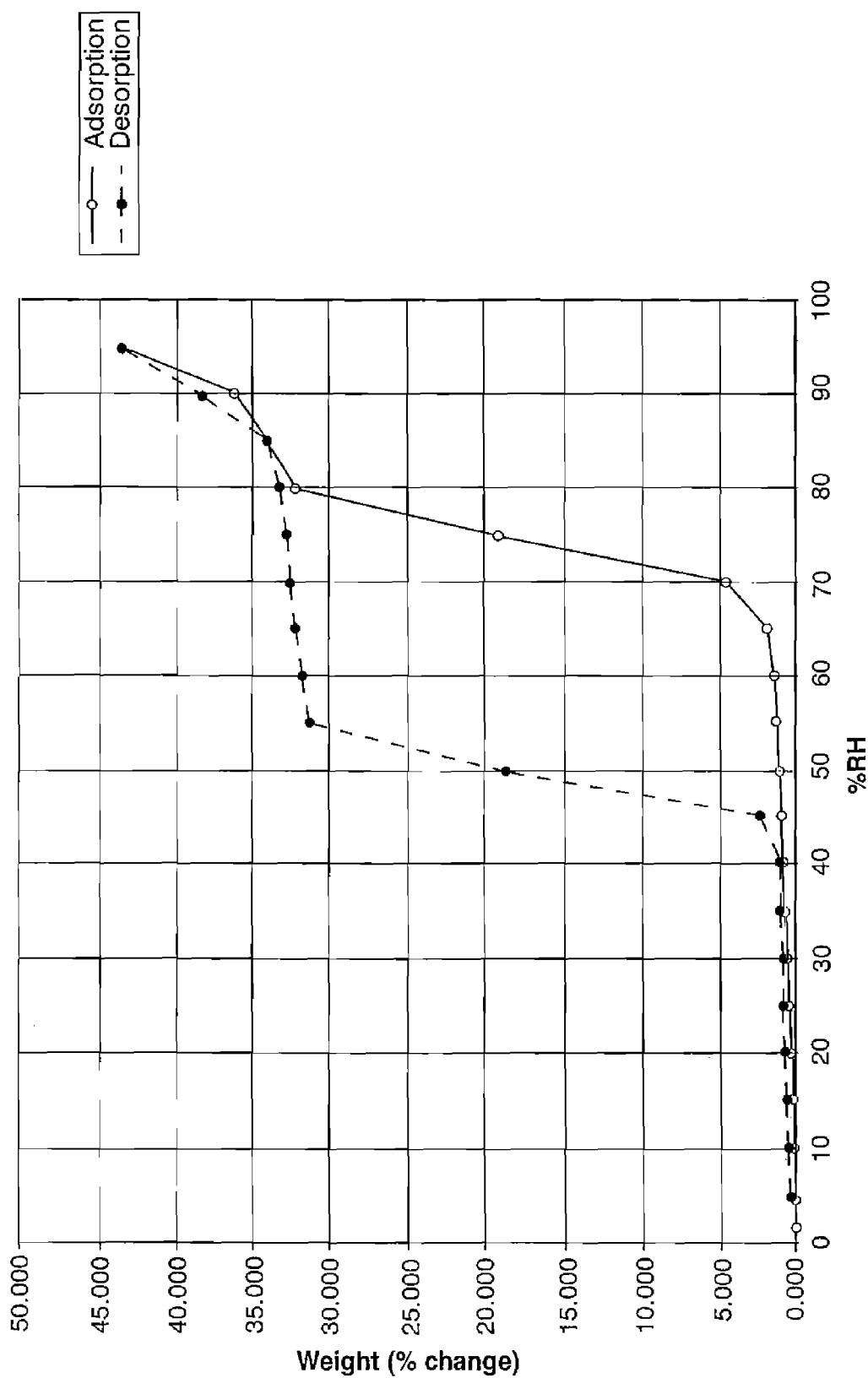
Figure 24:
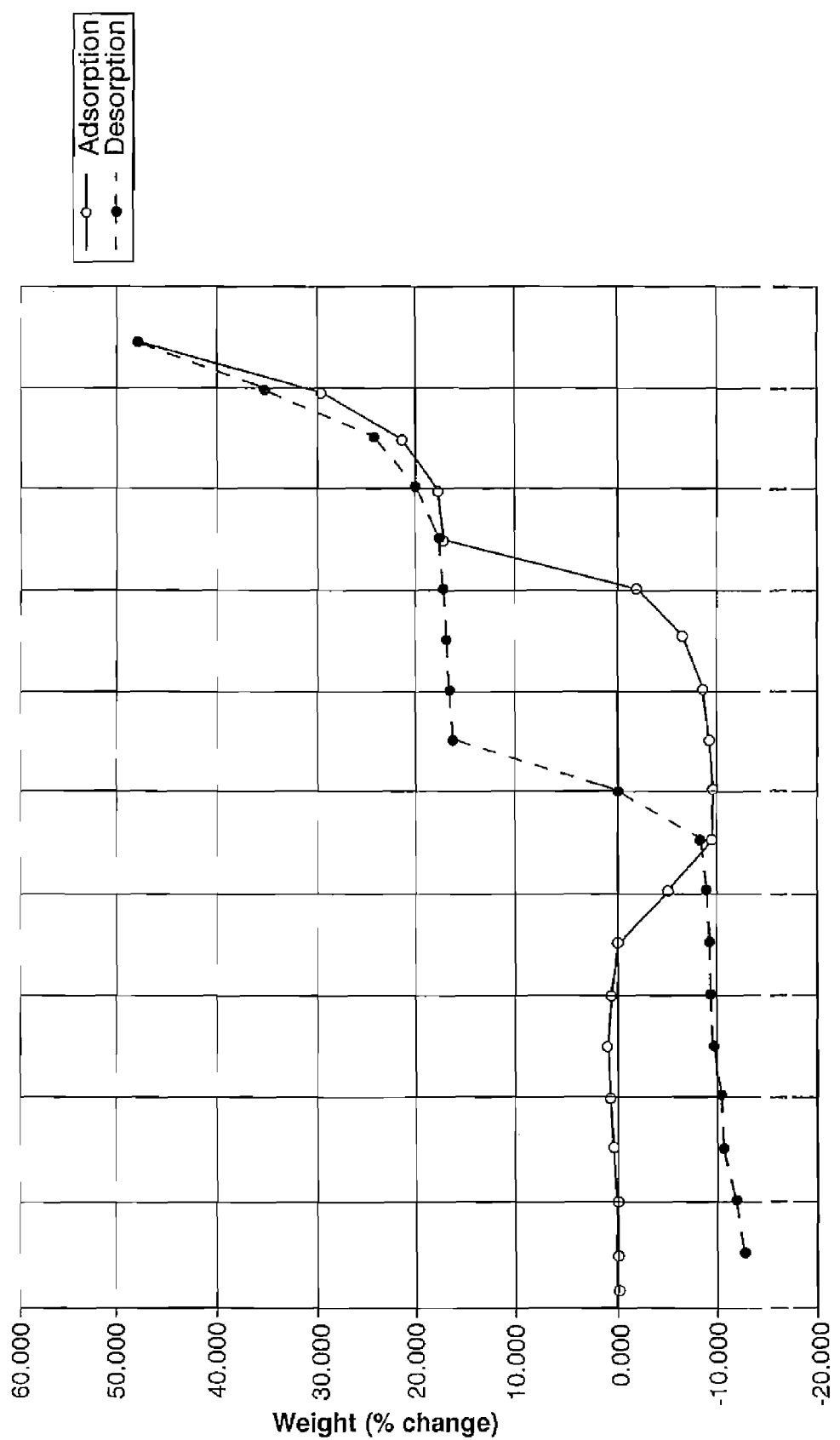
Figure 25:
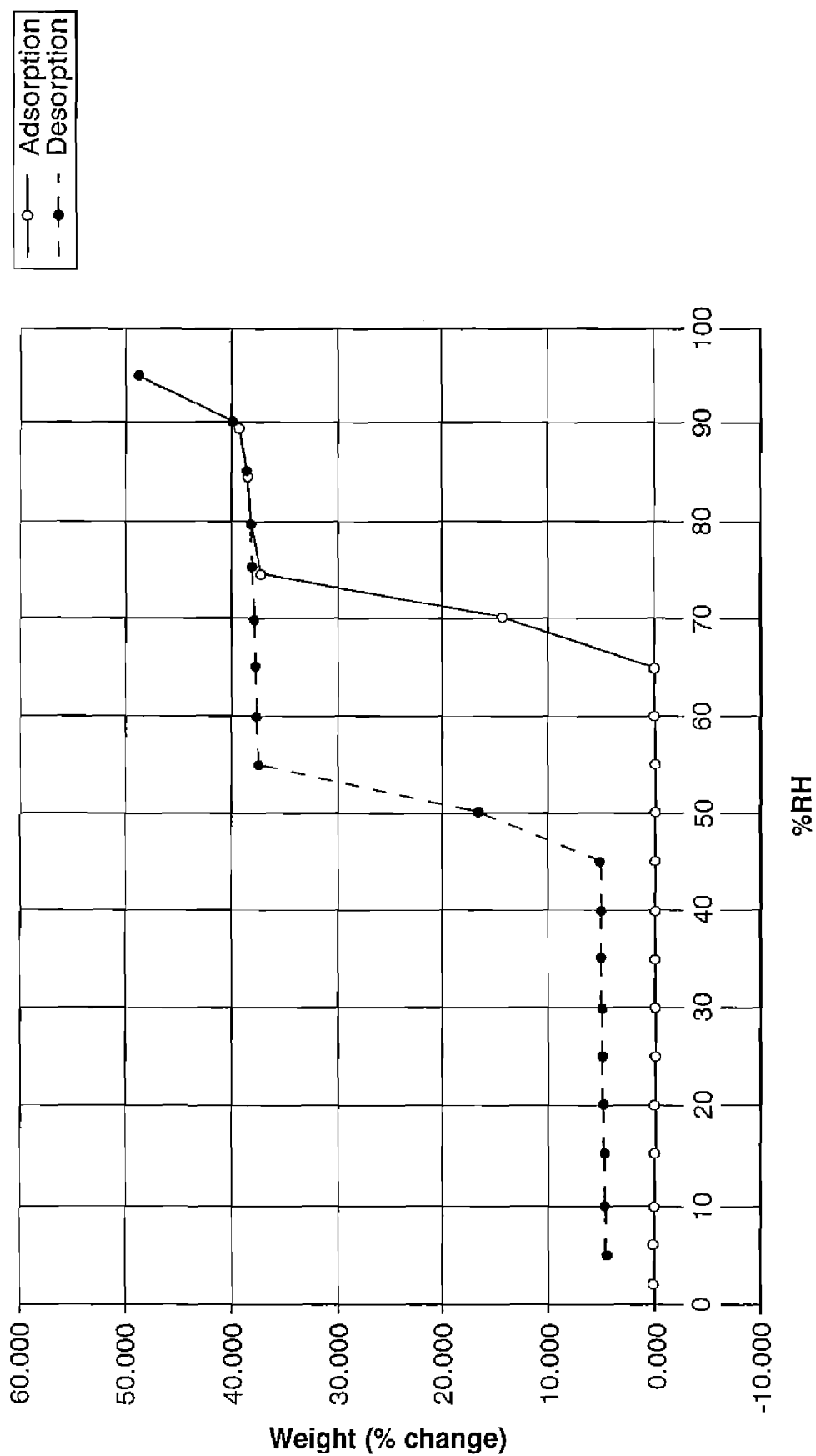

A 22 L, five neck round bottom flask, was equipped with an overhead stirrer, reflux condenser, thermocouple temperature read out, and heating mantle. The following reaction was run under a dry nitrogen atmosphere. Reagent acetone (13000 mL) and 4-[(4-chloro-2-hydroxy-benzoyl)amino]butanoic acid (500.0 g, 1.94 mol) were charged to the reactor and stirring was started. The reaction slurry was heated to 50° C. until a hazy brown solution was obtained. The warm solution was pumped through a warm pressure filter dressed with Whatman #1 paper into a clean 22 L reactor. The clear yellow filtrate was heated to 50° C. while stirring. Sodium hydroxide solution (50% aqueous; 155 g, 1.94 mol) was charged to the reactor while maintaining vigorous agitation. After the base addition was complete, the reactor was heated to reflux (60° C.) for 2.5 hours and then allowed to cool slowly to ambient temperature. The product was isolated by vacuum filtration through a sintered glass funnel and dried in a vacuum oven at 50° C. for 24 hours to give 527.3 g of sodium 4-[(4-chloro-2-hydroxybenzoyl)amino]butanoate as an off-white solid. Using acetone in the final stage of the synthesis always resulted in the production of the anhydrous crystalline form. The yield was 97.2%. The Form I prepared was a crystalline polymorph having a melting point onset of about 215.07° C. and characterized by an X-ray powder diffractogram substantially as shown in FIG. 1. A DSC scan, TGA spectrum, and Sorption/desorption curve of the Form I prepared are shown in FIGS. 6, 11, and 22, respectively. FTIR spectra of the Form I prepared are shown in FIGS. 16A and 16B.

EXAMPLE 1e

Preparation of Form II—Sodium 4-CNAB

A 22 L flask was equipped with an overhead stirrer. Deionized water (2000 mL) and 4-[(4-chloro-2-hydroxy-benzoyl) amino]butanoic acid (380.0 g, 1.47 mol) were added and stirring was started. A solution of sodium hydroxide (59.0 g, 1.48 mol) in water (500 mL) was added to the reactor. Water (1500 mL) was added to the reactor, and the resulting slurry was heated until a complete solution was obtained. The reaction mixture was cooled to ambient temperature, and then concentrated to dryness under reduced pressure. The resulting solids were scraped from the flask and vacuum dried at 50° C. to give 401.2 g of sodium 4-[4-chloro-2-hydroxybenzoyl)amino]butanoate as an off-white solid. The yield was 96.9%. The Form II prepared was a crystalline polymorph having a melting point onset of about 214.24° C. and characterized by an X-ray powder diffractogram substantially as shown in FIG. 2. A DSC scan, TGA, FTIR spectrum, and sorption/desorption curve of the Form II prepared are shown in FIGS. 7, 12A-12B, 17, and 23, respectively.

EXAMPLE 1f

Preparation of Form III—Sodium 4-CNAB Through the Isopropanol Solvate

A one liter, four neck round bottom flask was equipped with an overhead stirrer, reflux condenser, thermocouple temperature read out, and heating mantle. The following reaction was run under a dry nitrogen atmosphere. Isopropanol (400 mL) and 4-[(4-chloro-2-hydroxy-benzoyl)amino]butanoic acid (25.0 g, 0.09 mol) were charged to the reactor and stirring was started. The reaction slurry was heated to 50° C. until a hazy brown solution was obtained. The warm solution was filtered through a warm pressure filter dressed with Whatman #1 paper into a clean 1 L reactor. The clear yellow filtrate was heated to 62° C. while stirring. Sodium hydroxide solution (50% aqueous; 7.2 g, 0.09 mol) was charged to the reactor while maintaining vigorous agitation. After the base addition was complete, the reactor was heated to reflux (72° C.) and then allowed to cool slowly to ambient temperature. The product was isolated by vacuum filtration through a sintered glass funnel and vacuum dried at 50° C. for 24 hours to give 23.16 g of sodium 4-[(4-chloro-2-hydroxybenzoyl)amino] butanoate as an off-white solid. The yield was 92%.

The Form III prepared was a crystalline polymorph having a melting point onset of about 223.08° C. and characterized by an X-ray powder diffractogram substantially as shown in accompanying FIG. 3. A DSC scan, TGA spectrum, FTIR spectrum, and sorption/desorption curve of the Form III prepared are shown in FIGS. 8, 13, 18, and 24, respectively.

EXAMPLE 1g

Preparation of Form IV—Sodium 4-CNAB

Take Form I (Example 1d) or Form II (Example 1e) or Form V (Example 1h) of sodium 4-CNAB and expose the sample to a relative humidity of 75% or greater. Allow at least seven days of exposure at the high relative humidity until the X-ray diffraction pattern of a random sample of the material matches that of Form IV of sodium 4-CNAB.

Form IV was prepared by exposing Form I to a relative humidity of 90% for one week and then stored at a relative humidity of 80% for one week.

Figure 9:
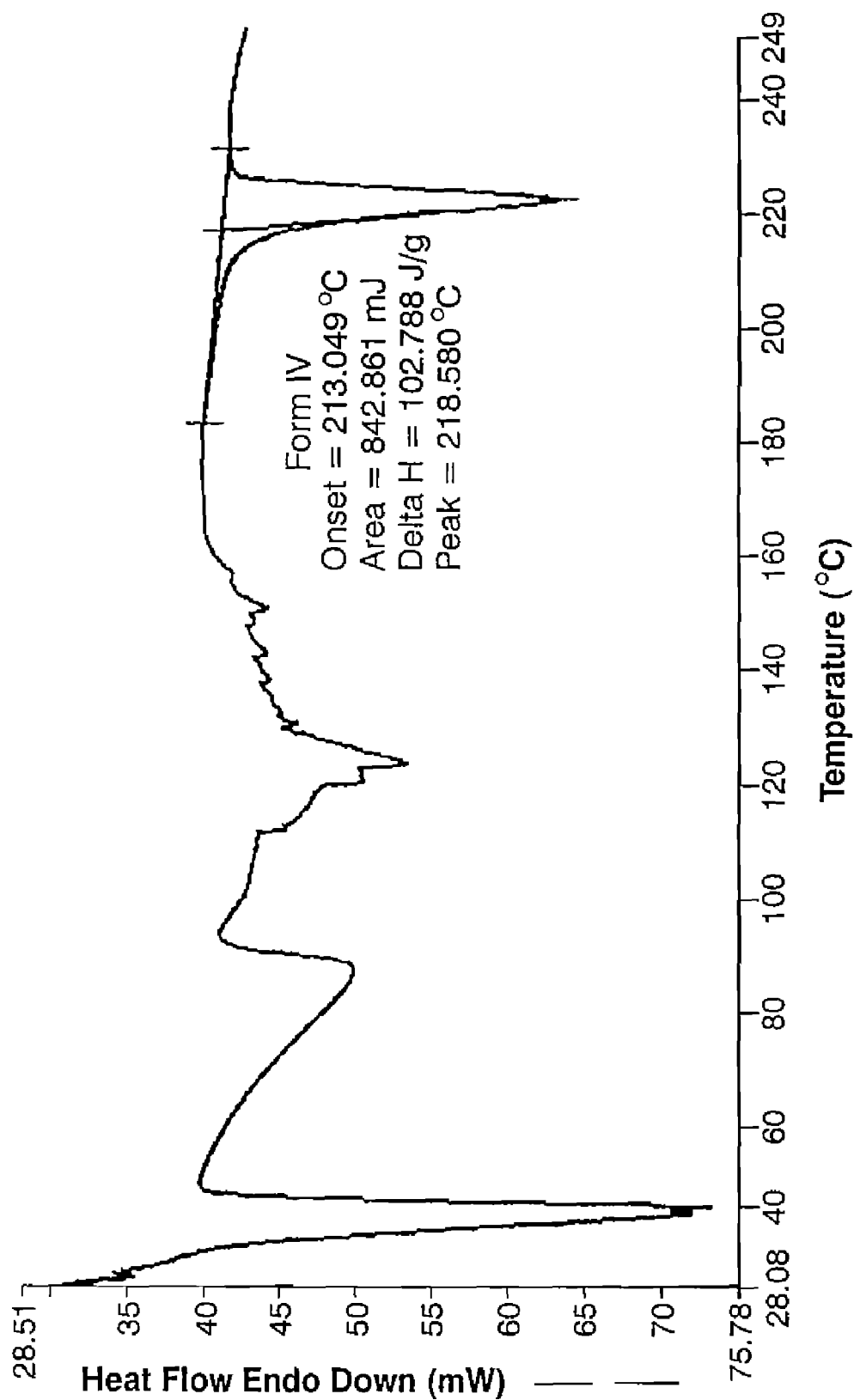
Figure 10:
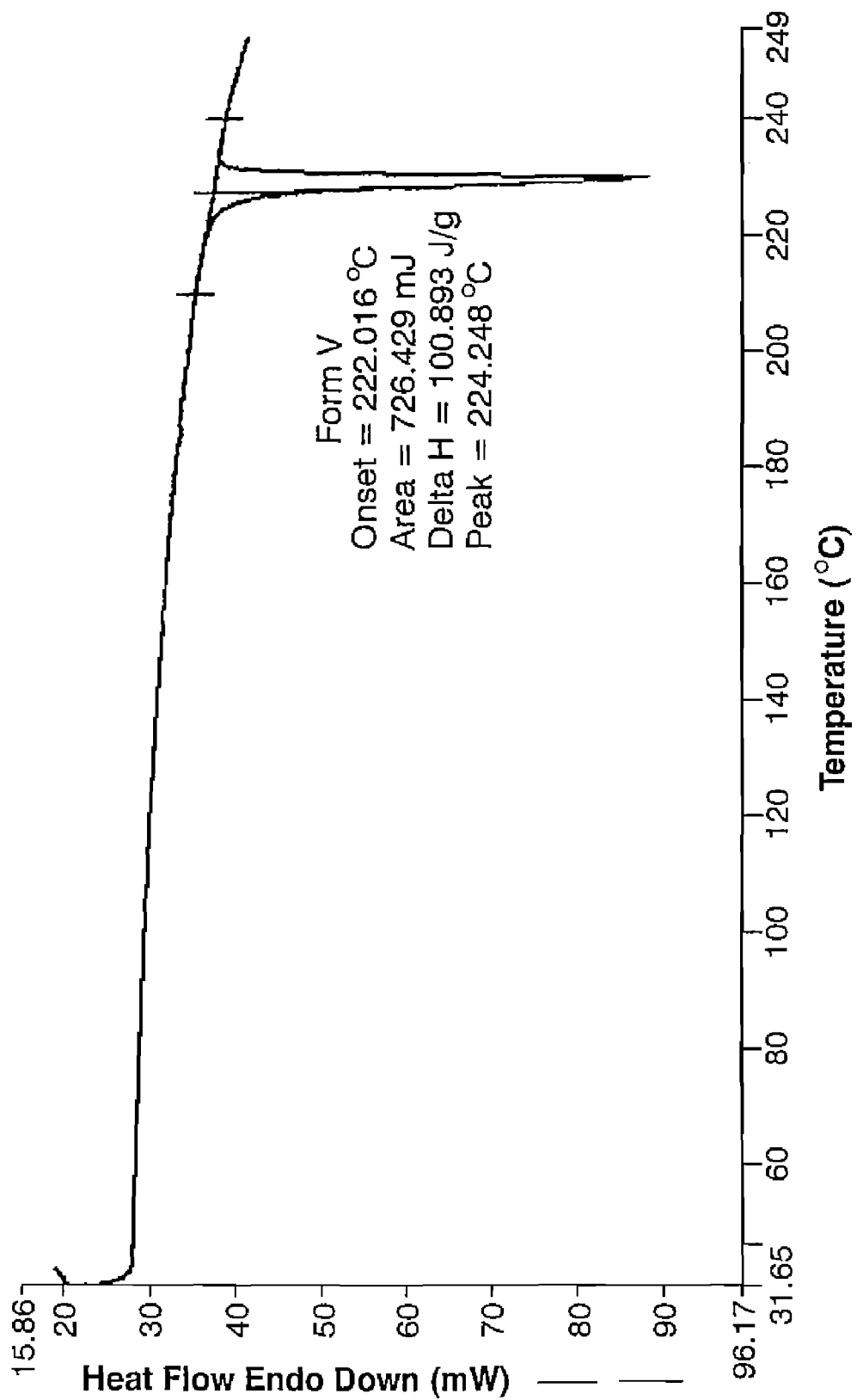
Figure 14:
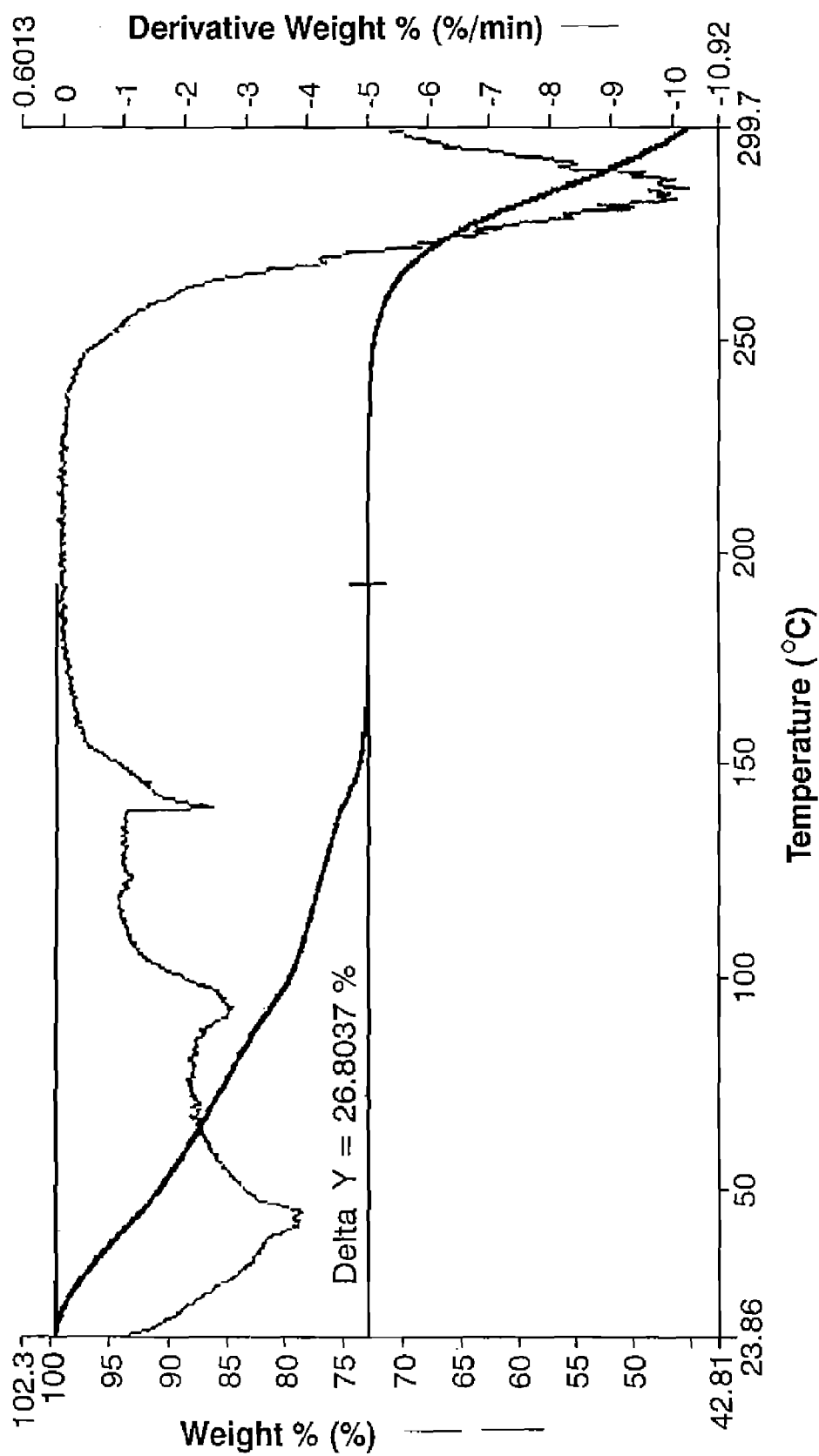
Figure 15:
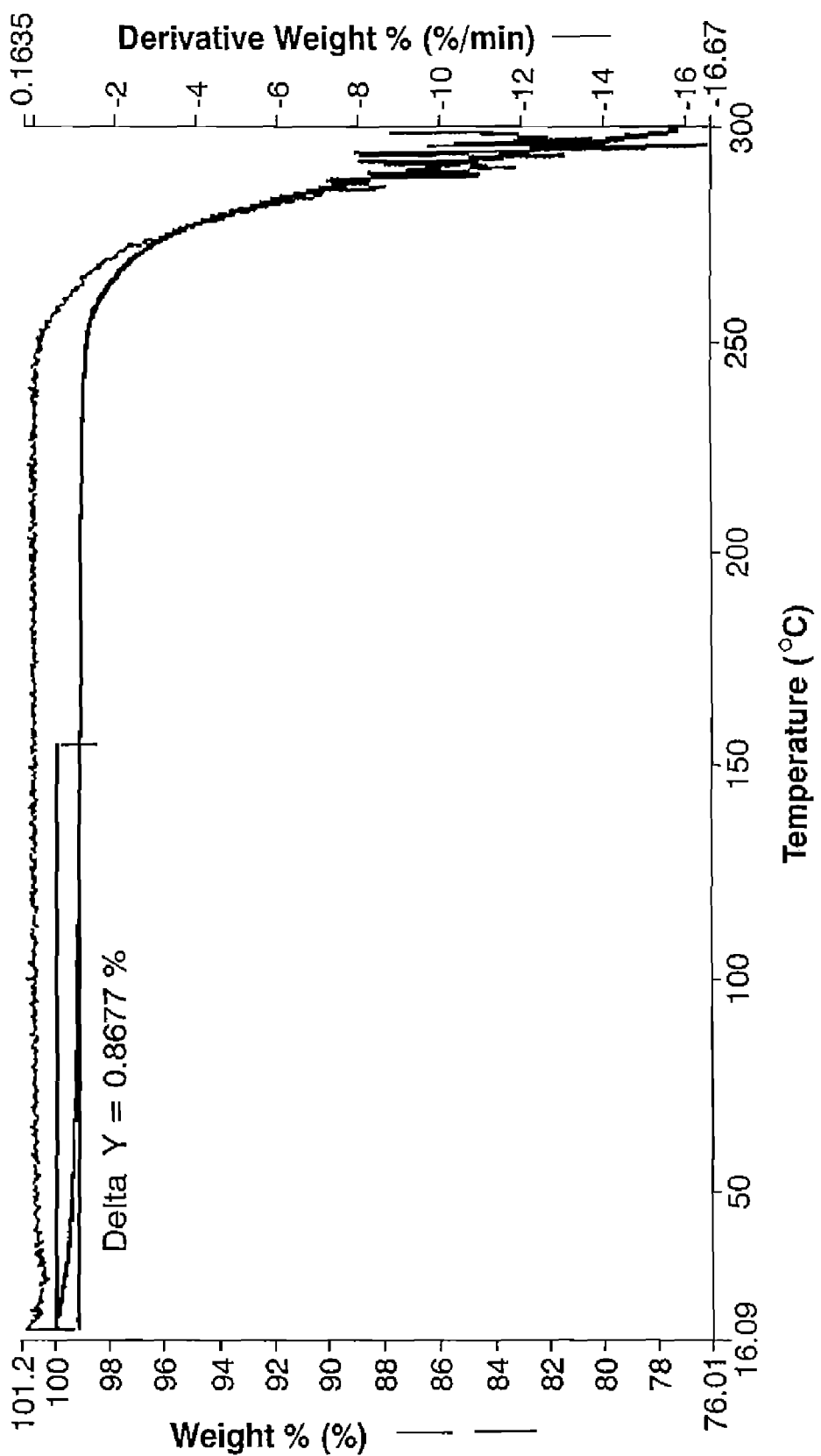
Figure 19:
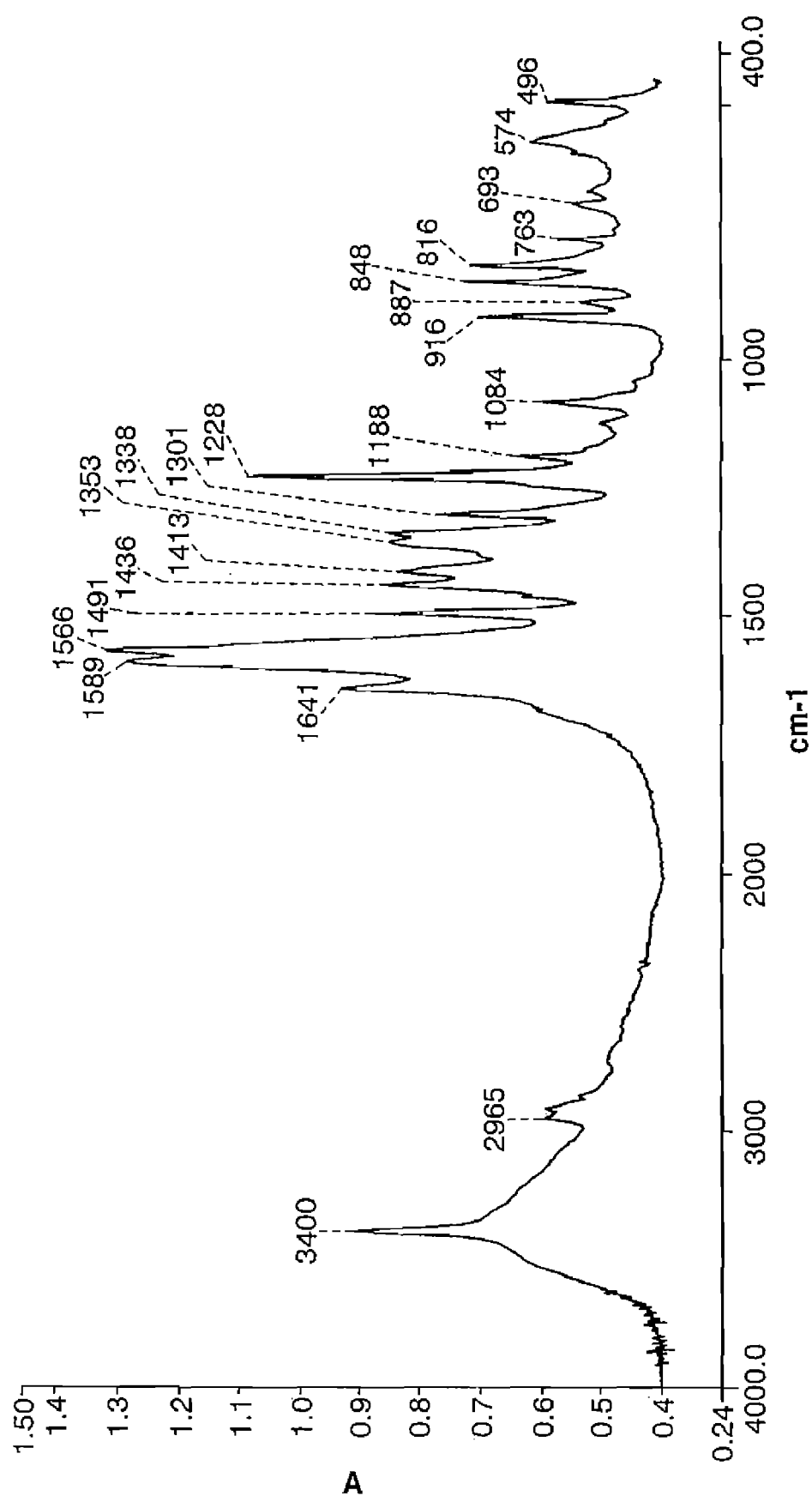
Figure 20:
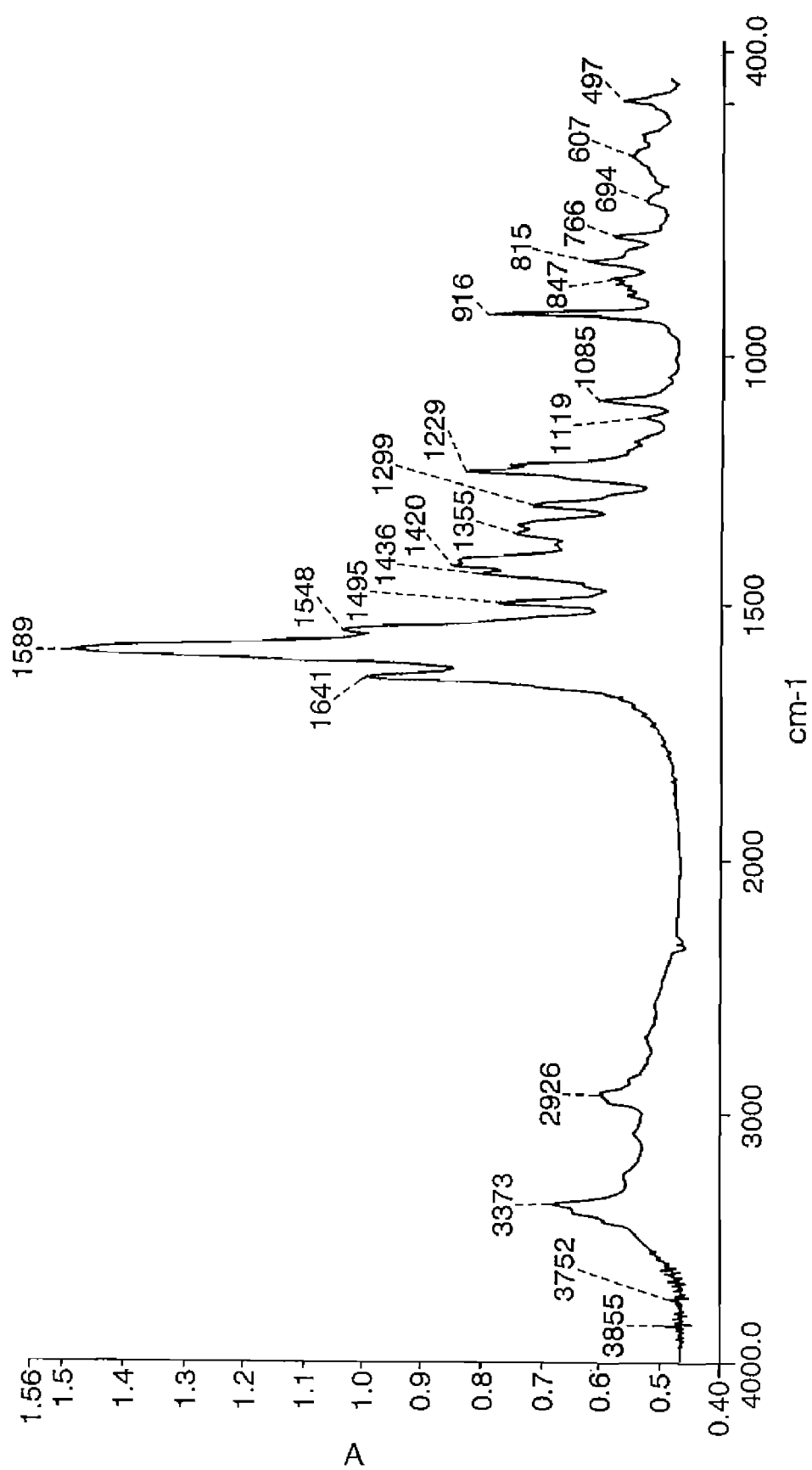

The Form IV prepared was a crystalline polymorph having a melting point onset of about 213.05° C. and characterized by an X-ray powder diffractogram substantially as shown in accompanying FIG. 4. A DSC scan, TGA spectrum, and FTIR spectrum of the Form IV prepared are shown in FIGS. 9, 14, and 19, respectively.

EXAMPLE 1h

Method of Preparation of Form V

Sodium 4-CNAB

Take a sample of Form III (Example 1f) of sodium 4-CNAB (the isopropanol solvate), and keep it in a dry air oven at a temperature greater than the solid state transition temperature of the desolvated material but lower than the melting temperature (the solid transition event occurs soon after desolvation at a heating rate of 10 deg. C./min (with an onset of about 137-144° C.)). Allow twelve to eighteen hours for the material to transform from the original form to Form V of sodium 4-CNAB. Continue the exposure to the high temperature until the X-ray diffraction pattern of a random sample of the material, tested after cooling, matches that of Form V.

Form V was prepared by heating Form III overnight in a dry air oven at 170° C. The Form V prepared was a crystalline polymorph having a melting point onset of about 222.02° C. and characterized by an X-ray powder diffractogram substantially as shown in accompanying FIG. 5. A DSC scan, TGA spectrum, FTIR spectrum, and sorption/desorption curve of the Form V prepared are shown in FIGS. 10, 15, 20, and 25.

EXAMPLE 1i

Method of Preparation of Amorphous Sodium 4-CNAB

Solidification

Form I of sodium 4-CNAB (anhydrous form) was heated to a temperature of 220° C. in a vacuum or nitrogen atmosphere until all of the sodium 4-CNAB was melted. The sodium 4-CNAB was then allowed to cool.

Heat any form of sodium 4-CNAB in an air-free atmosphere (e.g., vacuum or nitrogen atmosphere) at a temperature between its melting temperature and decomposition temperature for a time sufficient to melt the sodium 4-CNAB. Then cool the sodium 4-CNAB to yield it in amorphous form. Preferably, all of the sodium 4-CNAB is melted before cooling to yield a pure amorphous product.

From Solution:

Sodium 4-CNAB (20-40 mg) was treated with 100 µL IPA:H$_2$O (19:1, volume ratio) (IPA=isopropanol) until complete dissolution was attained. The resulting solution was filtered through a 0.2-µm nylon filter into a clean vial and left in a fume hood overnight at ambient temperature without cover (fast evaporation).

By Lyophilization:

5 g of sodium 4-CNAB was dissolved in 5 µL of deionized (DI) water. The solution was sonicated for 30 minutes at a bath temperature of 40° C. Then the solution was freeze dried at −43° C.

The amorphous form prepared by all of these methods was unstable at ambient conditions and transforms to Form II.

Figure 21:
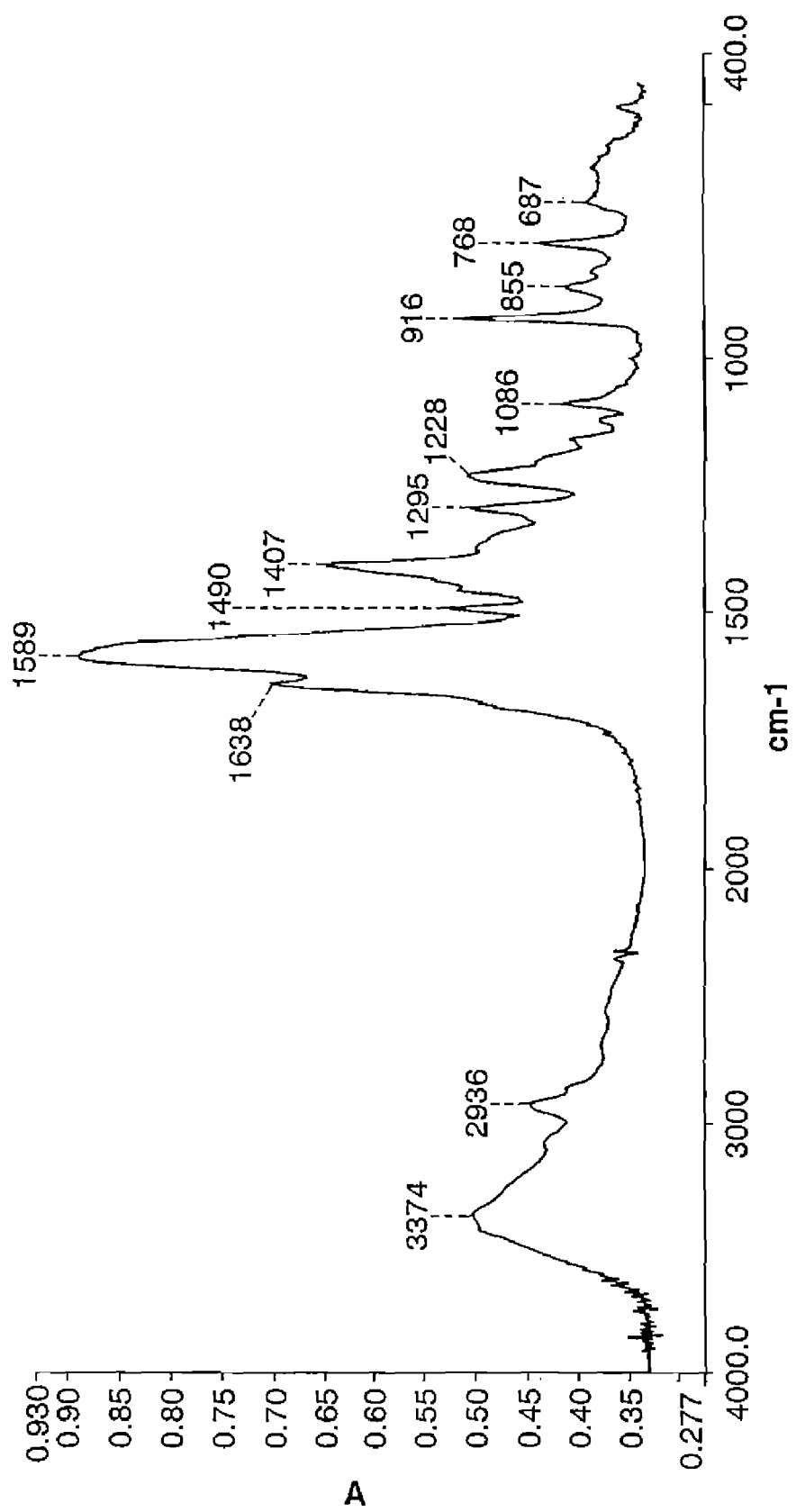
FIG. 21 is an FTIR spectrum of amorphous sodium 4-CNAB.
Figure 26:
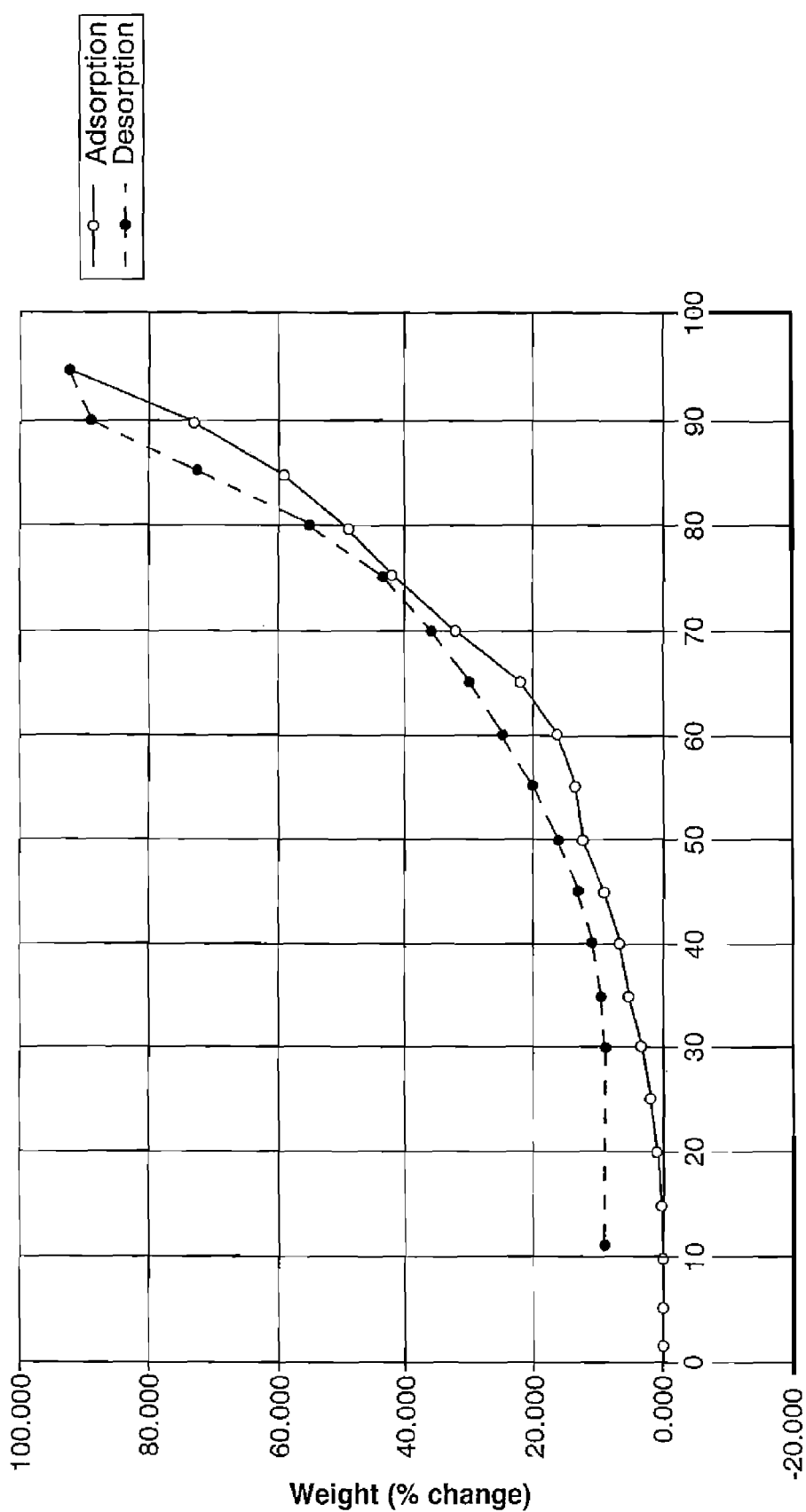
FIG. 26 is a moisture adsorption/desorption curve for amorphous sodium 4-CNAB.
Figure 27B:
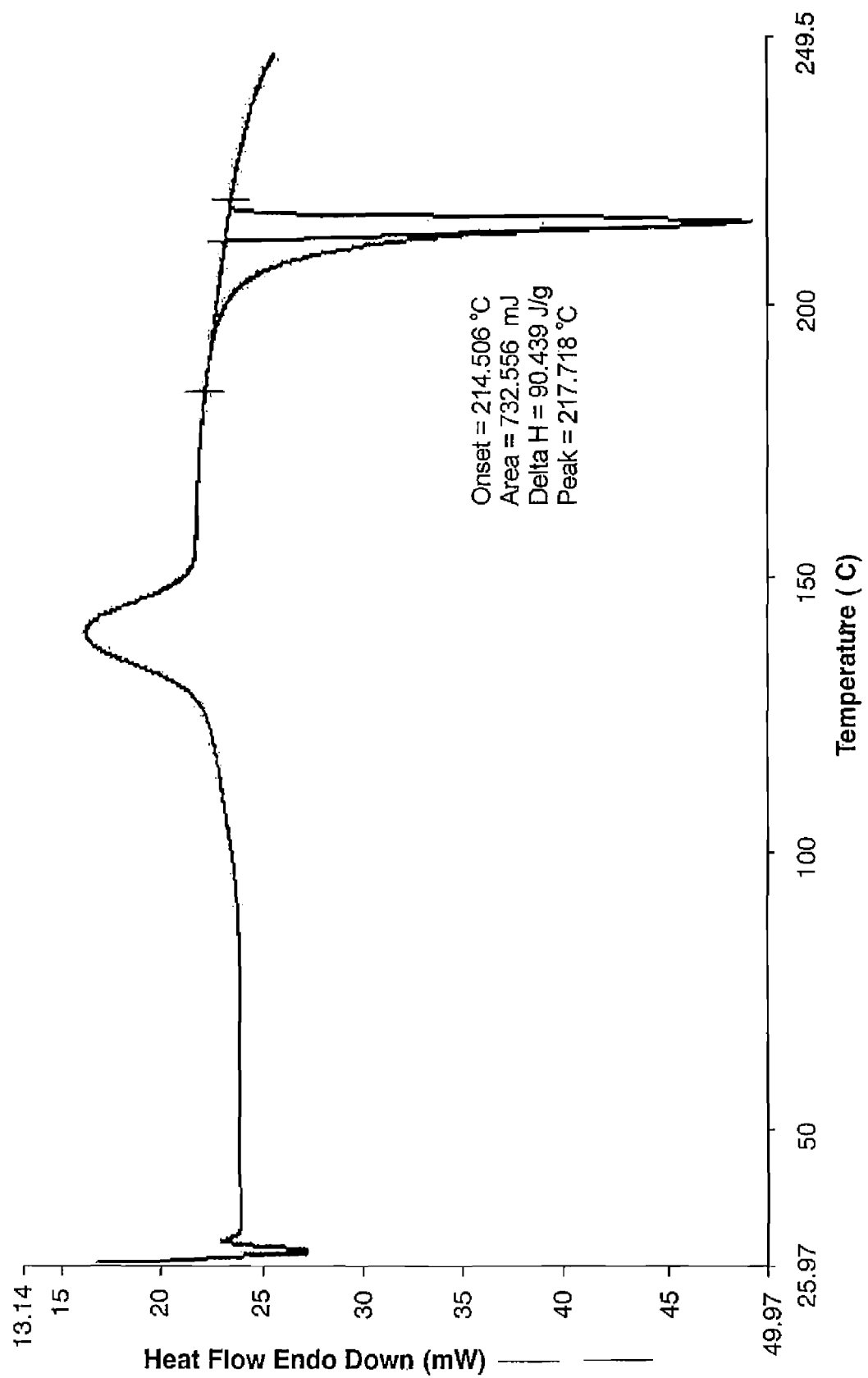
Figure 28:
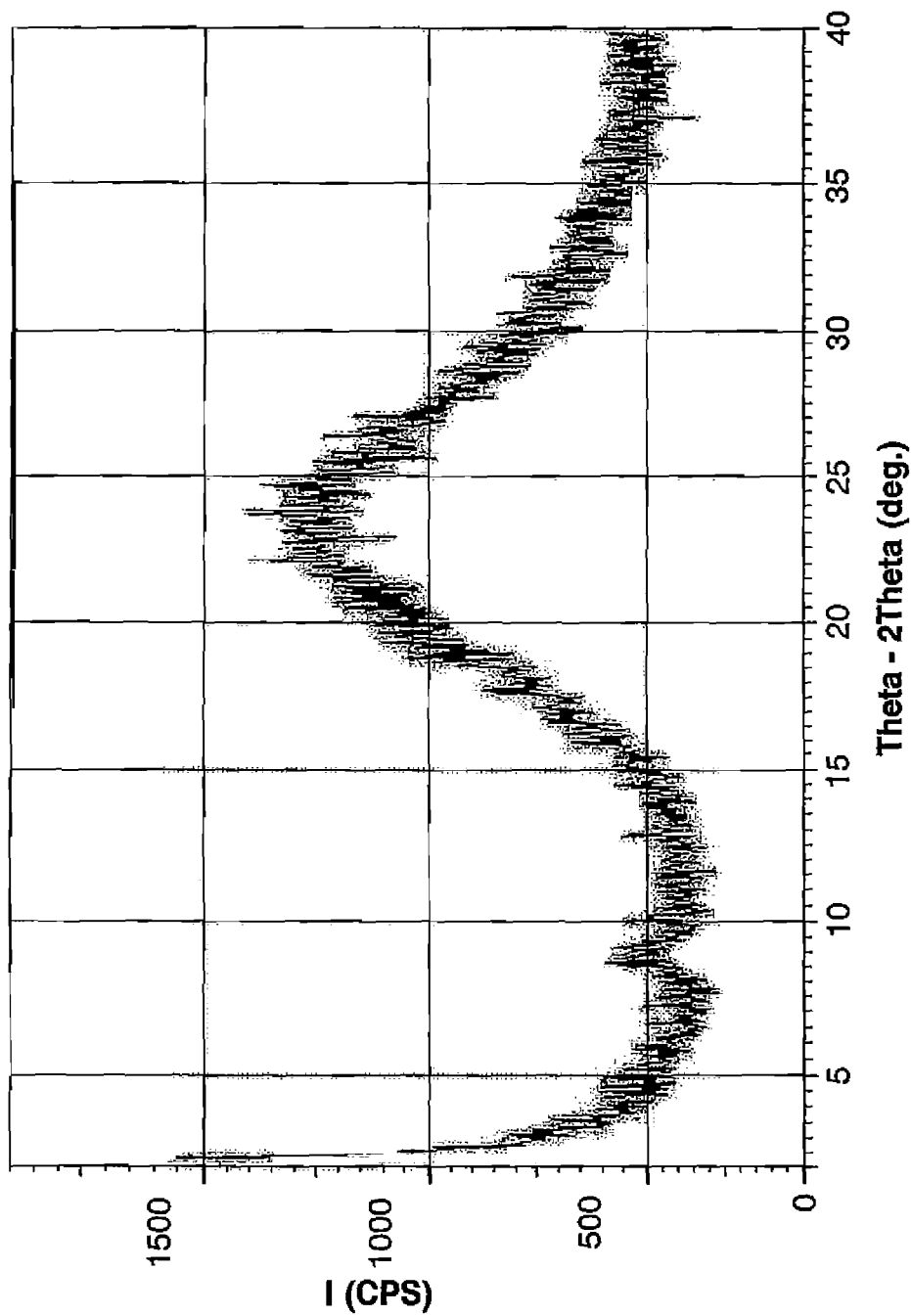
FIG. 28 is an XRPD of amorphous sodium 4-CNAB.

The amorphous form has a glass transition temperature at about 80-100° C. and may be characterized by an X-ray powder diffractogram substantially as shown in FIG. 28. DSC scans of the amorphous form prepared are shown in FIGS. 27A and 27B. An FTIR spectrum and sorption/desorption curve of the amorphous form prepared are shown in FIGS. 21 and 26, respectively.

EXAMPLE 1j

Capsule Preparation

Capsules for primate dosing containing the monosodium salt of compound I (as prepared in example 1d) and insulin were prepared as follows. The compound I monosodium salt and QA307X zinc insulin crystals human: proinsulin derived (recombinant DNA origin) (available from Eli-Lilly & Co. of Indianapolis, Ind.) were first screened through a 35 mesh Tyler standard sieve and the required amount weighed. Screened compound I monosodium salt and insulin were blended using geometric sieving method in a suitably sized glass mortar. The materials in the mortar were mixed well with a glass pestle. A spatula was used for scrapping the sides of the mortar. The resulting formulation was transferred to a plastic weigh boat for capsule filling. The formulation was hand packaged into size #0 Torpac hard gelatin capsules (available from Torpac, Inc. of Fairfield, N.J.). Each capsule fill weight was dependent on the individual animal weight. Capsules doses of compound I were 100 mg/kg, 75 mg/kg and 50 mg/kg (as monosodium salt). Capsule doses of insulin were 0.25 to 0.5 mg per kg.

EXAMPLE 2

Insulin—Oral Delivery

A. Rat Studies

Oral dosing (PO) compositions of delivery agent compound (prepared as in Example 1a or 1b as indicated below) and zinc human recombinant insulin (available from Calbiochem-Novabiochem Corp., La Jolla, Calif. (Catalog #407694)) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted. (For example, for compound 1a, a total of 258.5 ml 10N NaOH was added to 501 mg compound in 1.5 ml water, final pH 7.73.) Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The final delivery agent compound dose, insulin dose and dose volume amounts are listed below in Table 1.

The dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=15, 30, 60, 120 and 180 minutes after administration. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (μU/ml) were measured for each time point for each of the five animals in each dosing group. The five values for each time point were averaged and the results plotted as serum insulin concentration versus time. The maximum (peak) and the area under the curve (AUC) are reported below in Table 1. Previous experiments revealed no measurable levels of human insulin following oral dosing with human insulin alone.

TABLE 1

Insulin - Oral Delivery

| Compound | volume dose (ml/kg) | Compound Dose (mg/kg) | Insulin Dose (mg/kg) | Mean Peak Serum Human Insulin (μU/ml ± SE) | AUC |
|---|---|---|---|---|---|
| 1a | 1.0 | 200 | 0.5 | 1457 ± 268 | 58935 |
| 1b | 1.0 | 200 | 0.5 | 183 ± 89 | 8674 |
| 1b | 1.0 | 200 | 0.5 | 136 ± 52 | 5533 |
| 1b | 1.0 | 200 | 0.5 | 205 ± 61 | 7996 |
| 1b | 1.0 | 200 | 0.5 | 139 ± 43 | 5271 |

B. Monkey Studies

All animal protocols adhered to the "Principles of Laboratory Animal Care" and were Institutional Animal Care and Use Committee (IACUC) approved.

The dosing protocol for administering the capsules to each animal was as follows. Baseline plasma samples were obtained from the animals prior to dosing. Groups of four cynomolgus monkeys, two males and two females, weighing 2-3 kg were fasted for 4 hours prior to dosing and up to 2 hours after dosing. The animals were anesthetized with an intramuscular injection of 10 mg/kg ketamine hydrochloride immediately prior to dosing. Each animal was administered varying doses of compound I (25-100 mg/kg) in combination with varying doses of insulin 0.25-0.5 mg/kg insulin as 1 capsule. Water was available throughout the dosing period and 400 ml of juice was made available to the animal overnight prior to dosing and throughout the dosing period. The animal was restrained in a sling restraint. A capsule was placed into a pill gun, which is a plastic tool with a cocket plunger and split rubber tip to accommodate a capsule. The pill gun was inserted into the esophagus of the animal. The plunger of the pill gun was pressed to push the capsule out of the rubber tip into the espophagus. The pill gun was then retracted. The animals mouth was held closed and approximately 5 ml reverse osmosis water was administered into the mouth from the side to induce a swallowing reflex. The throat of the animal was rubbed further to induce the swallowing reflex.

Citrated blood samples (1 mL each) were collected by venipuncture from an appropriate vein at 1 hour before dosing and at 10, 20, 30, 40, and 50 minutes and 1, 1.5, 2, 3, 4, and 6 hours after dosing. Each harvested plasma sample was divided into two portions. One portion was frozen at −80° C. and shipped to another location for insulin assay. The other portion was used in the blood glucose assay. Four monkeys also received insulin subcutaneously (0.02 mg/kg). Blood samples were collected and analyzed as described above.

Insulin Assays. Serum insulin levels were measured using the Insulin ELISA Test Kit (DSL, Webster, Tex.).

Glucose Assays. Blood glucose measurements were performed using ONETOUCH® Glucose Monitoring System from Live Scan Inc., Newtown, Pa.

The results are shown in Table 1A below.

TABLE 1A

Insulin - Oral Delivery to Monkeys

| Compound | Compound Dose (mg/kg) | Insulin Dose (mg/kg) | Mean Peak Serum Human Insulin (μU/ml ± SE) | Mean Peak Blood Glucose Reduction (μU/ml ± SE) |
|---|---|---|---|---|
| 1d | 100 | 0.5 | 91.4 ± 45 | −52.3 ± 5.3 |
| 1d | 50 | 0.5 | 124.1 ± 51.95 | −61 ± 12.7 |
| 1d | 25 | 0.5 | 87.14 ± 53.85 | −28.75 ± 21.59 |
| 1d | 25 | 0.25 | 36.35 ± 32.3 | −19 ± 10.21 |

EXAMPLE 4

Cromolyn—Oral Delivery

Dosing solutions containing a delivery agent compound (prepared as in Example 1b) and cromolyn, disodium salt (cromolyn) (Sigma, Milwaukee, Wis.) were prepared in deionized water. The free acid of the delivery agent compound was converted to the sodium salt with one equivalent of sodium hydroxide. This mixture was vortexed and placed in a sonicator (about 37° C.). The pH was adjusted to about 7-7.5 with aqueous NaOH. Additional NaOH was added, if necessary, to achieve uniform solubility, and the pH re-adjusted. The mixture was vortexed to produce a uniform solution, also using sonication and heat if necessary. The delivery agent compound solution was mixed with cromolyn from a stock solution (175 mg cromolyn/ml in deionized water, pH adjusted, if necessary, with NaOH or HCl to about 7.0, stock solution stored frozen wrapped in foil, then thawed and heated to about 30° C. before using). The mixture was vortexed to produce a uniform solution, also using sonication and heat if necessary. The pH was adjusted to about 7-7.5 with aqueous NaOH. The solution was then diluted with water to the desired volume (usually 2.0 ml) and concentration and stored wrapped in foil before use. The final delivery agent compound and cromolyn doses, and the dose volumes are listed below in Table 2.

The typical dosing and sampling protocols were as follows. Male Sprague-Dawley rats weighing between 200-250 g were fasted for 24 hours and were anesthetized with ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected via the tail artery, typically at 0.25, 0.5, 1.0 and 1.5 hours after dosing. Serum cromolyn concentrations were measured by HPLC. Samples were prepared as follows: 100 µl serum was combined with 100 µl 3N HCl and 300 µl ethyl acetate in an eppendorf tube. The tube was vortexed for 10 minutes and then centrifuged for 10 minutes at 10,000 rpm. 200 ethyl acetate layer was transferred to an eppendorf tube containing 67 µl 0.1 M phosphate buffer. The tube was vortexed for 10 minutes and then centrifuged for 10 minutes at 10,000 rpm. The phosphate buffer layer was then transferred to an HPLC vial and injected into the HPLC (column=Keystone Exsil Amino 150×2 mm i.d., 5 µm, 100 Å (Keystone Scientific Products, Inc.); mobile phase=35% buffer (68 mM $KH_2PO_4$ adjusted to pH 3.0 with 85% $H_3PO_4$)/ 65% acetonitrile; injection volume=10 µl; flow rate=0.30 ml/minute; cromolyn retention time=5.5 minutes; absorbance detected at 240 nm). Previous studies indicated baseline values of about zero.

Results from the animals in each group were averaged for each time point and the highest of these averages (i.e., mean peak serum cromolyn concentration) is reported below in Table 2.

TABLE 2

Cromolyn - Oral Delivery

| Compound | volume dose (ml/kg) | Compound Dose (mg/kg) | Cromolyn Dose (mg/kg) | Mean Peak serum [cromolyn] ± SD (SE) |
|---|---|---|---|---|
| 1b | 1 | 200 | 25 | 0.70 ± 0.36 (0.16) |

EXAMPLE 4

Recombinant Human Growth Hormone (rhGH)—Oral Delivery

Oral gavage (PO) dosing solutions of delivery agent compound (prepared as in Example 1a or 1b as indicated in Table 3 below) and rhGH were prepared in phosphate buffer. The free acid of the delivery agent compound was converted to the sodium salt with one equivalent of sodium hydroxide. Typically, a solution of the compound was prepared in phosphate buffer and stirred, adding one equivalent of sodium hydroxide (1.0 N) when making the sodium salt. Additional NaOH was added, if necessary, to achieve uniform solubility, and the pH re-adjusted. The final dosing solutions were prepared by mixing the compound solution with an rhGH stock solution (15 mg rhGH/ml made by mixing as powders 15 mg rhGH, 75 mg D-mannitol, 15 mg glycine and 3.39 mg dibasic sodium phosphate, then diluting with 2% glycerol) and diluting to the desired volume (usually 3.0 ml). The compound and rhGH doses and the dose volumes are listed below in Table 3.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=15, 30, 45 and 60 minutes after administration. Serum rHGH concentrations were quantified by an rHGH immunoassay test kit (Kit # K1F4015 from Genzyme Corporation Inc., Cambridge, Mass.). Previous studies indicated baseline values of about zero.

Results from the animals in each group were averaged for each time point. The maximum of these averages (i.e., the mean peak serum rhGH concentration) is reported below in Table 3. (In the cases where no standard deviation (SD) or standard error (SE) is given below, the five samples from each time period were pooled prior to assaying.)

TABLE 3 rhGH - Oral Delivery

| Compound | Volume dose (ml/kg) | Compound Dose (mg/kg) | rhGH Dose (mg/kg) | Mean Peak Serum [rhGH] ± SD (SE) (ng/ml) |
|---|---|---|---|---|
| 1a | 1 | 200 | 3 | 99.35 |
| 1a | 1 | 200 | 3 | 42.62 |
| 1b | 1 | 200 | 3 | 84.01 ± 73.57 (32.90) |
| 1b | 1 | 200 | 3 | 50.44 ± 34.13 (15.26) |

EXAMPLE 5

Interferon—Oral Delivery

Dosing solutions of delivery agent compound (prepared as in Example 1b) and human interferon (IFN) were prepared in deionized water. The free acid of the delivery agent compound was converted to the sodium salt with one equivalent of sodium hydroxide. Typically, a solution of the delivery agent compound was prepared in water and stirred, adding one equivalent of sodium hydroxide (1.0 N) when making the sodium salt. This mixture was vortexed and placed in a sonicator (about 37° C.). The pH was adjusted to about 7.0 to 8.5 with aqueous NaOH. The mixture was vortexed to produce a uniform suspension or solution, also using sonication and heat if necessary. Additional NaOH was added, if necessary, to achieve uniform solubility, and the pH re-adjusted. The delivery agent compound solution was mixed with an IFN stock solution (about 22.0 to 27.5 mg/ml in phosphate buffered saline) and diluted to the desired volume (usually 3.0 ml). The final delivery agent compound and IFN doses, and the dose volumes are listed below in Table 4.

The typical dosing and sampling protocols were as follows. Male Sprague-Dawley rats weighing between 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. Solution was administered by pressing the syringe plunger.

Blood samples were collected serially from the tail artery, typically at time=0, 15, 30, 45, 60 and 90 minutes after administration. Serum IFN concentrations were quantified using Cytoscreen Immunoassay Kit for human IFN-alpha (catalog #KHC4012 from Biosource International, Camarillo, Calif.). Previous studies indicated baseline values of about zero. Results from the animals in each group were averaged for each time point. The maximum of these averages (i.e., the mean peak serum IFN concentration) is reported below in Table 4.

TABLE 4

Interferon - Oral Delivery

| Compound | Volume dose (ml/kg) | Compound Dose (mg/kg) | IFN Dose (mg/kg) | Mean Peak Serum [IFN] (ng/ml) ± SD (SE) |
|---|---|---|---|---|
| Form I | 1.0 | 200 | 1.0 | 17.80 ± 13.52 (6.05) |

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

The invention claimed is:

1. Form II of sodium 4-[(4-chloro-2-hydroxybenzoyl)-amino]-butanoate.

2. A crystalline hydrate of sodium 4-[(4-chloro-2-hydroxybenzoyl)-amino]butanoate exhibiting an X-ray powder diffraction pattern substantially as shown in FIG. 2.

3. A hydrate of sodium 4-[(4-chloro-2-hydroxybenzoyl)amino]butanoate exhibiting an X-ray powder diffraction pattern having peaks in degrees 2Θ±0.2° 2Θ at 10.2, 18.3, 19.5, 19.8, 21.8, 23.5, 26.3, 27.8, 29.4, and 31.8.

4. The crystalline polymorph of claim 3, wherein the hydrate has a melting point onset as determined by differential scanning calorimetry at about 214.24° C.

5. A crystalline polymorph of an isopropanol solvate of sodium 4-[(4-chloro-2-hydroxybenzoyl)amino]butanoate exhibiting an X-ray powder diffraction pattern substantially as shown in FIG. 3.

6. A crystalline polymorph of an isopropanol solvate of sodium 4-[(4-chloro-2-hydroxybenzoyl)amino]butanoate exhibiting an X-ray powder diffraction pattern having peaks in degrees 2Θ±0.2° 2Θ at 5.5, 10.8, 11.9, 16.3, 17.3, 21.7, 24.7, 25.0, 26.1, and 26.4.

7. The crystalline polymorph of claim 6, wherein the crystalline polymorph has a melting point onset as determined by differential scanning calorimetry at about 223.08° C.

8. A method of preparing Form II of sodium 4-[(4-chloro-2-hydroxybenzoyl)amino]butanoate comprising the steps of:
(a) dissolving 4-[(4-chloro-2-hydroxybenzoyl)-amino]butanoic acid in water to form an aqueous solution;
(b) adding a sodium source to the aqueous solution to Form II of sodium 4-[(4-chloro-2-hydroxybenzoyl)amino]butanoate.

9. A method of preparing Form II of sodium 4-[(4-chloro-2-hydroxybenzoyl)amino]butanoate comprising the step of exposing Form III, Form V, or amorphous sodium 4-[(4-chloro-2-hydroxybenzoyl)amino]butanoate or a mixture thereof to an effective amount of moisture for a sufficient time to Form II of sodium 4-[(4-chloro-2-hydroxybenzoyl)amino]butanoate.

10. A method of preparing Form II of sodium 4-[(4-chloro-2-hydroxybenzoyl)amino]butanoate comprising the step of drying Form IV of sodium 4-[(4-chloro-2-hydroxybenzoyl)amino]butanoate in an environment having less than about 55% relative humidity.

11. A method of preparing Form III of sodium 4-[(4-chloro-2-hydroxybenzoyl)amino]butanoate comprising the sequential steps of:
(a) dissolving 4-[(4-chloro-2-hydroxybenzoyl)-amino]butanoic acid in isopropanol to form a solution;
(b) heating the solution to above room temperature;
(c) adding a sodium source to the solution;
(d) heating the solution to reflux; and
(e) cooling the solution to yield Form III of sodium 4-[(4-chloro-2-hydroxybenzoyl)amino]butanoate.

* * * * *